US010709755B2

(12) United States Patent
Ando et al.

(10) Patent No.: US 10,709,755 B2
(45) Date of Patent: *Jul. 14, 2020

(54) SOLID FORMULATION AND METHOD FOR PREVENTING OR REDUCING COLORATION THEREOF

(71) Applicant: Elobix AB, Gothenburg (SE)

(72) Inventors: Takahiko Ando, Kawasaki (JP);
Hirokazu Hagio, Kawasaki (JP);
Takashi Matsushita, Kawasaki (JP);
Yusuke Ito, Kawasaki (JP)

(73) Assignee: Elobix AB, Göteborg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/320,621

(22) PCT Filed: Jun. 24, 2015

(86) PCT No.: PCT/JP2015/068242
§ 371 (c)(1),
(2) Date: Dec. 20, 2016

(87) PCT Pub. No.: WO2015/199147
PCT Pub. Date: Dec. 30, 2015

(65) Prior Publication Data
US 2017/0143783 A1 May 25, 2017

(30) Foreign Application Priority Data
Jun. 25, 2014 (JP) ................. 2014-130092

(51) Int. Cl.
A61K 31/554 (2006.01)
A61K 9/28 (2006.01)
A61K 9/20 (2006.01)
A61K 38/05 (2006.01)

(52) U.S. Cl.
CPC ............ *A61K 38/05* (2013.01); *A61K 9/2009* (2013.01); *A61K 9/2018* (2013.01); *A61K 9/2054* (2013.01); *A61K 9/2068* (2013.01); *A61K 9/284* (2013.01); *A61K 9/2853* (2013.01); *A61K 9/2866* (2013.01); *A61K 31/554* (2013.01)

(58) Field of Classification Search
CPC ....... A61K 38/05; A61K 9/2866; A61K 9/284
See application file for complete search history.

(56) References Cited

U.S. PATENT DOCUMENTS

| 3,539,380 | A | 11/1970 | Johnson |
| 4,172,120 | A | 10/1979 | Todd et al. |
| 4,507,235 | A | 3/1985 | Wunsch |
| 5,167,965 | A | 12/1992 | Schulz |
| 5,294,448 | A | 3/1994 | Ring |
| 5,422,124 | A | 6/1995 | Valducci |
| 5,681,584 | A | 10/1997 | Savastano |
| 5,811,388 | A | 9/1998 | Friend et al. |
| 5,900,233 | A | 5/1999 | Day |
| 5,976,811 | A | 11/1999 | Mullner et al. |
| 5,994,391 | A | 11/1999 | Lee et al. |
| 6,069,167 | A | 5/2000 | Sokol |
| 6,277,831 | B1 | 8/2001 | Frick et al. |
| 6,346,527 | B1 | 2/2002 | Takanaka et al. |
| 6,355,672 | B1 | 3/2002 | Yasuma et al. |
| 6,387,924 | B2 | 5/2002 | Lee et al. |
| 6,387,944 | B1 | 5/2002 | Frick et al. |
| 6,426,340 | B1 | 7/2002 | Gibson et al. |
| 6,592,900 | B1 | 7/2003 | Buhler |
| 6,635,280 | B2 * | 10/2003 | Shell ..................... A61K 9/0065 424/464 |
| 6,676,979 | B2 | 1/2004 | Marlett et al. |
| 6,906,058 | B2 | 6/2005 | Starke et al. |
| 6,943,189 | B2 | 9/2005 | Keller et al. |
| 7,019,023 | B2 | 3/2006 | Frick et al. |
| 7,125,864 | B2 | 10/2006 | Starke et al. |
| 7,132,416 | B2 | 11/2006 | Starke et al. |
| 7,132,557 | B2 | 11/2006 | Wilkes et al. |
| 7,192,945 | B2 | 3/2007 | Starke et al. |
| 7,192,946 | B2 | 3/2007 | Starke et al. |
| 7,192,947 | B2 | 3/2007 | Starke et al. |
| 7,226,943 | B2 | 6/2007 | Starke et al. |
| 7,238,684 | B2 | 7/2007 | Starke et al. |
| 7,514,421 | B2 | 4/2009 | Abrahamsson et al. |

(Continued)

FOREIGN PATENT DOCUMENTS

| CA | 2065151 | 3/1991 |
| DE | 3930168 | 3/1991 |

(Continued)

OTHER PUBLICATIONS

U.S. Appl. No. 15/230,124, filed Aug. 5, 2016, Gillberg et al.
U.S. Appl. No. 15/726,071, filed Oct. 5, 2017, Gillberg et al.
U.S. Appl. No. 15/722,110, filed Oct. 2, 2017, Gillberg et al.
U.S. Appl. No. 15/726,203, filed Oct. 5, 2017, Gillberg et al.
U.S. Appl. No. 15/894,472, filed Feb. 12, 2018, Gillberg et al.
U.S. Appl. No. 15/976,584, filed May 10, 2018, Gillberg et al.
U.S. Appl. No. 15/988,560, filed May 24, 2018, Gillberg et al.
U.S. Appl. No. 15/988,688, filed May 24, 2018, Gillberg et al.
U.S. Appl. No. 15/988,281, filed May 24, 2018, Gillberg et al.
U.S. Appl. No. 15/988,317, filed May 24, 2018, Gillberg et al.
U.S. Appl. No. 15/988,210, filed May 24, 2018, Gillberg et al.

(Continued)

Primary Examiner — Kortney L. Klinkel
(74) Attorney, Agent, or Firm — Fish & Richardson P.C.

(57) ABSTRACT

The present invention relates to stabilization of a certain benzothia(dia)zepine derivative in a solid formulation containing the same. In the present invention, in a solid formulation containing the benzothia(dia)zepine derivative mentioned above, a combination of polyethylene glycol and polyvinyl alcohol is not blended, or alternatively, in the case of blending polyethylene glycol and polyvinyl alcohol in the solid formulation, the aforementioned derivative is isolated from the combination of polyethylene glycol and polyvinyl alcohol.

15 Claims, No Drawings

(56) References Cited

U.S. PATENT DOCUMENTS

| | | |
|---|---|---|
| 7,767,229 B1 | 8/2010 | Milne et al. |
| 7,923,468 B2 | 4/2011 | Frick et al. |
| 7,939,061 B2 | 5/2011 | Prakash et al. |
| 8,048,413 B2 | 11/2011 | Huguet |
| 8,067,584 B2 | 11/2011 | Starke et al. |
| 9,023,368 B2 | 5/2015 | Basit et al. |
| 9,295,677 B2 | 3/2016 | Ling et al. |
| 9,684,018 B2 | 6/2017 | Horanzy |
| 9,694,018 B1 | 7/2017 | Gillberg et al. |
| 9,701,649 B2 | 7/2017 | Bohlin et al. |
| 9,745,276 B2 | 8/2017 | Bohlin et al. |
| 9,872,844 B2 | 1/2018 | Zernel et al. |
| 2002/0054903 A1 | 5/2002 | Tyler et al. |
| 2002/0142054 A1 | 10/2002 | Marlett et al. |
| 2003/0124088 A1 | 7/2003 | Masuda et al. |
| 2003/0125316 A1 | 7/2003 | Keller et al. |
| 2003/0143183 A1 | 7/2003 | Knudsen et al. |
| 2003/0153541 A1 | 8/2003 | Dudley et al. |
| 2003/0215843 A1 | 11/2003 | Poupon et al. |
| 2004/0014806 A1 | 1/2004 | Bhat et al. |
| 2004/0038862 A1 | 2/2004 | Goodwin et al. |
| 2004/0062745 A1 | 4/2004 | Green et al. |
| 2004/0067933 A1 | 4/2004 | Starke et al. |
| 2004/0077625 A1 | 4/2004 | Tremont et al. |
| 2004/0082647 A1 | 4/2004 | Babiak et al. |
| 2004/0176438 A1 | 9/2004 | Tremont et al. |
| 2005/0009805 A1 | 1/2005 | Sasahara et al. |
| 2005/0089572 A1 | 4/2005 | Kumar |
| 2005/0113362 A1 | 5/2005 | Lindstedt et al. |
| 2005/0118326 A1 | 6/2005 | Anfinsen |
| 2005/0124557 A1 | 6/2005 | Lindqvist |
| 2005/0171204 A1 | 8/2005 | Lindstedt et al. |
| 2005/0197376 A1 | 9/2005 | Kayakiri et al. |
| 2005/0215882 A1 | 9/2005 | Chenevert et al. |
| 2005/0266080 A1* | 12/2005 | Desai .................. A61K 9/2086 424/472 |
| 2005/0282822 A1 | 12/2005 | Alstermark et al. |
| 2006/0083790 A1 | 4/2006 | Anderberg et al. |
| 2006/0210631 A1 | 9/2006 | Patel |
| 2006/0210633 A1 | 9/2006 | Dharmadhikari |
| 2007/0197522 A1 | 8/2007 | Edwards et al. |
| 2007/0237818 A1 | 10/2007 | Malcom et al. |
| 2008/0193543 A1 | 8/2008 | Morello |
| 2008/0207592 A1 | 8/2008 | Frick et al. |
| 2008/0300171 A1 | 12/2008 | Balkan et al. |
| 2009/0098200 A1 | 4/2009 | Temtsin Krayz et al. |
| 2009/0131395 A1 | 5/2009 | Antonelli et al. |
| 2010/0130472 A1 | 5/2010 | Young et al. |
| 2010/0286122 A1 | 11/2010 | Belyk |
| 2011/0003782 A1 | 1/2011 | Pellicciari |
| 2011/0152204 A1 | 6/2011 | Gedulin et al. |
| 2011/0159087 A1 | 6/2011 | Sathe et al. |
| 2011/0294767 A1 | 12/2011 | Gedulin et al. |
| 2012/0114588 A1* | 5/2012 | Starke .................. A61K 31/554 424/78.01 |
| 2012/0157399 A1 | 6/2012 | Young et al. |
| 2013/0029938 A1 | 1/2013 | Aquino et al. |
| 2013/0052269 A1 | 2/2013 | Lescure |
| 2013/0059807 A1 | 3/2013 | Gedulin et al. |
| 2013/0108573 A1 | 5/2013 | Gedulin et al. |
| 2013/0109671 A1 | 5/2013 | Gedulin et al. |
| 2013/0225511 A1 | 8/2013 | Gillberg et al. |
| 2013/0236541 A1 | 9/2013 | Gillberg et al. |
| 2015/0031636 A1 | 1/2015 | Gillberg et al. |
| 2015/0031637 A1 | 1/2015 | Gillberg et al. |
| 2016/0039777 A1 | 2/2016 | Bohlin et al. |
| 2016/0146715 A1 | 5/2016 | Shim et al. |
| 2016/0193277 A1 | 7/2016 | Gillberg et al. |
| 2016/0194353 A1 | 7/2016 | Gillberg et al. |
| 2016/0229822 A1 | 8/2016 | Bohlin |
| 2016/0237049 A1 | 8/2016 | Bohlin |
| 2017/0143738 A1 | 5/2017 | Ando et al. |
| 2017/0182115 A1 | 6/2017 | Gillberg et al. |
| 2017/0224719 A1 | 8/2017 | Gillberg et al. |
| 2017/0224720 A1 | 8/2017 | Gillberg et al. |
| 2017/0224721 A1 | 8/2017 | Gillberg et al. |
| 2017/0240516 A1 | 8/2017 | Ymen et al. |
| 2018/0022776 A1 | 1/2018 | Gillberg et al. |
| 2018/0030088 A1 | 2/2018 | Gillberg et al. |
| 2018/0030089 A1 | 2/2018 | Gillberg et al. |
| 2018/0140219 A1 | 5/2018 | Yin et al. |
| 2018/0030009 A1 | 6/2018 | Gillberg et al. |
| 2018/0264029 A1 | 9/2018 | Gillberg et al. |
| 2018/0264030 A1 | 9/2018 | Gillberg et al. |
| 2018/0264031 A1 | 9/2018 | Gillberg et al. |
| 2018/0360869 A1 | 12/2018 | Gillberg et al. |
| 2018/0360870 A1 | 12/2018 | Gillberg et al. |
| 2018/0360871 A1 | 12/2018 | Gillberg et al. |
| 2018/0362577 A1 | 12/2018 | Gillberg et al. |
| 2019/0046451 A1 | 2/2019 | Gillberg et al. |
| 2019/0070217 A1 | 3/2019 | Gillberg et al. |

FOREIGN PATENT DOCUMENTS

| | | |
|---|---|---|
| DE | 19825804 | 8/2000 |
| EP | 0278464 | 8/1988 |
| EP | 0489423 | 12/1991 |
| EP | 0372542 | 10/1992 |
| EP | 0573848 | 5/1993 |
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0594570 | 7/1995 |
| EP | 0864582 | 9/1998 |
| EP | 1173205 | 4/2000 |
| EP | 1045840 | 10/2000 |
| EP | 1273307 | 1/2003 |
| EP | 1535913 | 6/2005 |
| EP | 1719768 | 11/2006 |
| EP | 2144599 | 2/2008 |
| EP | 3210977 | 8/2017 |
| GB | 1573487 | 8/1980 |
| GB | 2262888 | 7/1996 |
| JP | 2000-513028 | 10/2000 |
| JP | A-2004/516285 | 6/2004 |
| JP | B-3665055 | 6/2005 |
| JP | 2006/124695 | 5/2006 |
| JP | B-4870552 | 2/2012 |
| JP | 2013-541584 | 11/2013 |
| JP | A-2013-542953 | 11/2013 |
| JP | B-5421326 | 2/2014 |
| WO | WO 1991/03249 | 3/1991 |
| WO | WO 93/16055 | 8/1993 |
| WO | WO 94/00111 | 1/1994 |
| WO | WO 94/18183 | 8/1994 |
| WO | WO 94/18184 | 8/1994 |
| WO | WO 96/05188 | 2/1996 |
| WO | WO 96/08484 | 3/1996 |
| WO | WO 96/16051 | 5/1996 |
| WO | WO 97/33882 | 9/1997 |
| WO | WO 98/03818 | 1/1998 |
| WO | WO 98/07449 | 1/1998 |
| WO | WO 98/38182 | 9/1998 |
| WO | WO 98/40375 | 9/1998 |
| WO | WO 1998/56757 | 12/1998 |
| WO | WO 99/01149 | 1/1999 |
| WO | WO 99/32478 | 1/1999 |
| WO | WO 99/35135 | 7/1999 |
| WO | WO 99/64409 | 7/1999 |
| WO | WO 99/64410 | 12/1999 |
| WO | WO 00/01687 | 1/2000 |
| WO | WO 00/38725 | 7/2000 |
| WO | WO 00/38726 | 7/2000 |
| WO | WO 00/38727 | 7/2000 |
| WO | WO 00/38728 | 7/2000 |
| WO | WO 00/38729 | 7/2000 |
| WO | WO 00/47568 | 8/2000 |
| WO | WO 00/61568 | 10/2000 |
| WO | WO 00/62810 | 10/2000 |
| WO | WO 2001/34570 | 5/2001 |
| WO | WO 01/60807 | 8/2001 |
| WO | WO 01/66533 | 9/2001 |

(56) References Cited

FOREIGN PATENT DOCUMENTS

| | | |
|---|---|---|
| WO | WO 01/68096 | 9/2001 |
| WO | WO 01/68637 | 9/2001 |
| WO | WO 02/08211 | 1/2002 |
| WO | WO 02/09815 | 4/2002 |
| WO | WO 02/32428 | 4/2002 |
| WO | WO 02/50051 | 6/2002 |
| WO | WO 02/53548 | 6/2002 |
| WO | WO 03/020710 | 3/2003 |
| WO | WO 03/022286 | 3/2003 |
| WO | WO 03/022804 | 3/2003 |
| WO | WO 03/022825 | 3/2003 |
| WO | WO 03/022830 | 3/2003 |
| WO | WO 2003/043992 | 5/2003 |
| WO | WO 03/051821 | 6/2003 |
| WO | WO 03/051822 | 6/2003 |
| WO | WO 03/061663 | 7/2003 |
| WO | WO 03/091232 | 11/2003 |
| WO | WO 03/106482 | 11/2003 |
| WO | WO 04/006899 | 1/2004 |
| WO | WO 04/056748 | 7/2004 |
| WO | WO 04/076430 | 9/2004 |
| WO | WO 04/089350 | 9/2004 |
| WO | WO 04/020421 | 10/2004 |
| WO | WO2004/089350 | 10/2004 |
| WO | WO 2005/082874 | 9/2005 |
| WO | WO 07/009655 | 1/2007 |
| WO | WO 07/009656 | 1/2007 |
| WO | WO 08/058628 | 5/2008 |
| WO | WO 08/058630 | 5/2008 |
| WO | WO 08/058631 | 5/2008 |
| WO | WO 10/062861 | 6/2010 |
| WO | WO 2010/041268 | 9/2010 |
| WO | WO 11/137135 | 11/2011 |
| WO | WO 11/150286 | 12/2011 |
| WO | WO 12/064267 | 5/2012 |
| WO | WO 12/064268 | 5/2012 |
| WO | WO 13/063512 | 5/2013 |
| WO | WO 13/063526 | 5/2013 |
| WO | WO 2014/174066 | 10/2014 |
| WO | WO 2015/193788 | 12/2015 |
| WO | WO 2017/138876 | 8/2017 |
| WO | WO 2017/138877 | 8/2017 |
| WO | WO 2017/138878 | 8/2017 |
| WO | WO 2019/032027 | 2/2019 |

OTHER PUBLICATIONS

U.S. Appl. No. 15/988,202, filed May 24, 2018, Gillberg et al.
AASLD: 2017 68th Annual Meeting of the American Association for the Study of Liver Diseases, Washington, DC, Oct. 20-24, 2017, (Abstract only).
Alvarez, Fernando; "Treatments in chronic cholestasis in children." Ann. Nestlé (2008) 66 p. 127-135.
Anakk et al., "Bile acids activate YAP to promote liver carcinogenesis," Cell Rep., Nov. 27, 2013, 5(4):1060-1069.
Angulo et al., "Independent Predictors of Liver Fibrosis in Patients With Nonalcoholic Steatohepatitis," Hepatology, Dec. 1999, 30(6): 1356-1362.
Balbach et al., "Pharmaceutical evaluation of early development candidates "the 100 mg-approach"," Int J Pharm, May 4, 2004, 275(1):1□12.
Baumann, U. et al., "The ileal bile acid transport inhibitor A4250 decreases pruritus and serum bile acids in cholestatic liver diseases—an ongoing multiple dose, open-label, multicenter study," Hepatology, 2017, 66(1): S91 (Abstract only).
Brunt et al., "Nonalcoholic Steatohepatitis: A Proposal for Grading and Staging the Histological Lesions," American Jounral of Gastroenterology, Sep. 1999, 94(9): 2467-2474.
Caira, "Crystalline Polymorphism of Organic Compounds," in: Topics in Current Chemistry, Jan. 1998, 198:163□208.
Ekkehard Sturm et al. The ileal bile acid transport inhibitor A4250 reduced pruritus and serum bile acid levels in children with cholestatic liver disease and pruritus: final results from a multiple-dose, open-label, multinational study Hepatology 2017; 66: 646-47 (Suppl. 1). doi: 10.1002/hep.29501.
Forner et al., "Treatment of hepatocellular carcinoma," Critical Reviews in Oncology/Hematology, 2006, 60:89-98.
Guzman et al., "Does Nonalcoholic Fatty Liver Disease Predispose Patients to Hepatocellular Carcinoma in the Absence of Cirrhosis?" Archives of pathology & laboratory medicine, Nov. 2008, 132(11):1761-1766.
hepc.liverfoundation.org' [online]. "Nonalcoholic Fatty Liver Disease," Brochure, 2016 [retrieved on Feb. 1, 2018]. Retrived from the Internet: URL<http://hepc.liverfoundation.org/wp-content/uploads/2012/07/NAFLD-Brochure-2016.pdf>, 8 pages.
Hollands et al., "Ileal exclusion for Byler's disease: an alternative surgical approach with promising early results for pruritus," Journal of Pediatric Surgery, Feb. 1988, 33(2): 220-224.
International Preliminary Report on Patentability for Application No. PCT/JP2015/068240, dated Jan. 5, 2017, 12 pages (with English translation).
International Preliminary Report on Patentability for International Application No. PCT/EP2015/074573, dated Apr. 25, 2017, 8 pages.
International Search Report and Written Opinion for Application No. PCT/SE2017/050127, dated May 8, 2017, 16 pages.
International Search Report and Written Opinion for International Application No. PCT/EP2015/074573, dated Apr. 28, 2016, 11 pages.
Jiang et al., "Non alcoholic steatohepatitis a precursor for hepatocellular carcinoma development," World Journal of Gastroenterology: WJG, Nov. 28, 2014, 20(44):16464-16473.
Mouzaki and Allard, "Non-alcoholic steatohepatitis: the therapeutic challenge of a global epidemic," Annals of Gastroenterology, 2012, 25: 207-217.
Perumpail et al., "Clinical epidemiology and disease burden of nonalcoholic fatty liver disease," World Journal of Gastroenterology, Dec. 2017, 23(47): 8263-8276.
Satapathy and Sanyal, "Epidemiology and Natural History of Nonalcoholic Fatty Liver Disease," Seminars in Liver Disease, Aug. 2015, 35(3): 221-235.
Scheuer, "Primary Biliary Cirrhosis," Proc. R. Soc. Med., Dec. 1967, 60:1257-1260.
Singhal et al., "Drug polymorphism and dosage form design: a practical perspective," Adv Drug Deliv Rev, Feb. 23, 2004, 56(3):335□347.
Sun et al., "Bile acids promote diethylnitrosamine-induced hepatocellular carcinoma via increased inflammatory signaling," American Journal of Physiology—Gastrointestinal and Liver Physiology, May 5, 2016, 311(1):G91-104.
Wang et al., "Increased hepatocellular carcinoma risk in chronic hepatitis B patients with persistently elevated serum total bile acid: a retrospective cohort study," Scientific reports, Dec. 1, 2016, 6:38180, 9 pages.
Xie et al., "Dysregulated hepatic bile acids collaboratively promote liver carcinogenesis," Int J Cancer, Oct. 15, 2016, 139(8):1764-1775.
"A Long-Term, Open-Label Study of LUM001 With a Double-Blind, Placebo Controlled, Randomized Drug Withdrawal Period to Evaluate Safety and Efficacy in Children With Alagille Syndrome (ICONIC)," Clinical Trials.gov, Jun. 9, 2014, retrieved Oct. 3, 2014, http://clinicaltrials.gov/ct2/show/NCT02160782?term=LUM001&rank=7, 4 pages.
"Alagile Syndrome," Wikipedia, the free encyclopedia, posted on or about Feb. 11, 2005, retrieved Feb. 12, 2014, http://en.wikipedia.org/wiki/Alagille_syndrome, 3 pages.
"Albireo's Lead Compound in Cholestatic Liver Diseases, A4250, Projects Against Bile Acid-Mediated Cholestatic Liver Injury in Mice," Albireo Press Release, Apr. 11, 2014, 2 pages.
"An Extension Study to Evaluate the Long-Term Safety and Durability of Effect of LUM001 in the Treatment of Cholestatic Liver Disease in Subjects With Alagille Syndrome (IMAGINE)," Clinical Trials.gov, Jan. 23, 2014, retrieved on Oct. 3, 2014, http://clinicaltrials.gov/ct2/show/NCT02047318?term=LUM001&rank=3, 3 pages.
"An Extension Study to Evaluate the Long-Term Safety and Durability of Effect of LUM001 in the Treatment of Cholestatic Liver

(56) References Cited

OTHER PUBLICATIONS

Disease in Subjects With Alagille Syndrome (IMAGINE-II)," Clincal Trials.gov, Apr. 16, 2014, retrieved on Oct. 3, 2014, http://clinicaltrials.gov/ct2/show/NCT02117713?term=LUM001&rank=2, 3 pages.
"Bowel Diversion Surgeries: Ileostomy, Colostomy, Ileoanal Reservoir and Continent Ileostomy," US Department of Health and Human Services: National Institute of Diabetes and Digestive and Kidney Diseases, Feb. 2009, retrieved on Jan. 27, 2014, http://digestive.niddk.nih.gov/ddiseases/pub/ileostomy/Bowel_Diversion_508.pdf, 4 pages.
"EASL Clinical Practice Guidelines: Management of cholestatic liver diseases," European Assoc. for the Study of the Liver, Journal of Hepatology, 2009, 51:237-267.
"Evaluation of LUM001 in the Reduction of Pruritus in Alagille Syndrome (ITCH)," Clinical Trials.gov, Feb. 5, 2014, retrieved on Oct. 3, 2014, http://clinicaltrials.gov/ct2/show/NCT02057692?term=LUM001&rank=5, 4 pages.
"IBAT inhibitor A4250 for Cholestatic Pruritus," ClinicalTrials.gov, Last updated Feb. 10, 2015, https://clinicaltrials.gov/ct2/show/NCT02360852?term=a4250&rank=1, 3 pages.
"Initiation of a Phase II Trial for A4250, the Company's Lead Compound for Cholestatic Liver Diseases and NASH," Albireo Pharma Press Release, Feb. 5, 2015, http://www.alberiopharma.com/News.aspx?PageID=1600872, 2 pages.
"Lumena Pharmaceuticals Now Dosing Patients in the INDIGO Phase 2 Clinical Trial of LUM001 in Pediatric Patients with Progressive Familial Intrahepatic Cholestasis," PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.
"Open Label Study to Evaluate Efficacy and Long Term Safety of LUM001 in the Treatment of Cholestatic Liver Disease in Patients With Progressive Familial Intrahepatic Cholestasis (INDIGO)," Clinical Trials.gov, Feb. 5, 2014, retrieved on Oct. 3, 2014, http://clinicaltrials.gov/ct2/show/NCT02057718?term=LUM001&rank=4, 3 pages.
"Open Label Study to Evaluate Safety and Efficacy of LUM001 in Patients With Primary Sclerosing Cholangitis (CAMEO)," Clinical Trials.gov, Feb. 11, 2014, retrieved Oct. 3, 2014, http://clinicaltrials.gov/ct2/show/NCT02061540?term=LUM001&rank=6, 3 pages.
"Phase 2 Study to Evaluate LUM001 in Combination With Ursodeoxycholic Acid in Patients With Primary Biliary Cirrhosis (CLARITY)," Clinical Trials.gov, Jul. 17, 2013, retrieved Oct. 3, 2014, http://clinicaltrials.gov/ct2/show/NCT01904058?term=LUM001&rank=8, 3 pages.
"Progressive familial intrahepatic cholestasis," Wikipedia, the free encyclopedia, posted on or about Feb. 24, 2006, http://en.wikipedia.org/wiki/Progressive_familial_intrahepatic_cholestasis, 3 pages.
"Safety and Efficacy Study of LUM001 in the Treatment of Cholestatic Liver Disease in Patients With Alagille Syndrome (IMAGO)," Clinical Trials.gov, Jul. 16, 2013, http://clinicaltrials.gov/ct2/show/NCT01903460?term=LUM001&rank=1, 3 pages.
"What is Alagille Syndrome?," European Medicines Agency, Jan. 21, 2014, retrieved on Oct. 3, 2014, http://www.ema.europa.eu/docs/en_GB/document_library/Orphan_designation/2014/01/WC500159874.pdf, 6 pages.
Alissa et al., "Invited Review: Update on Progressive Familial Intrahepatic Cholestasis," *Journal of Pediatric Gastroenterology and Nutrition*, 2008, 46:241-252.
American Diabetes Association, "Management of Dyslipidemia in Adults with Diabetes," Diabetes Care, Jan. 2003, 26(1).
Angulo, "Use of ursodeoxycholic acid in patients with liver disease," Current Gastroenterology Reports, Feb. 1, 2002, 4(1):37-44.
Artursson and Karlsson, "Correslation Between Oral Drug Absorption in Humans and Apparent Drug Permeability Coefficients in Human Intestinal Epithelial (CACO-2) Cells," Biochemical and Biophysical Research Communications, Mar. 1991, 175(3):880-885.
Attili et al., "Bile Acid-induced Liver Toxicity: Relation to the Hydrophobic-Hydrophilic Balance of Bile Acids," Medical Hypotheses, 1986, 19:57-69.
Baghdasaryan et al., "Inhibition of intestinal bile acid absorption by ASBT inhibito A4250 protects against bile acid-mediated cholestatic liver injury in mice," J. Hepatology, 2014, 60:S57.
Baghdasaryan et al., "Inhibition of intestinal bile acid absorption by ASBT inhibito A4250 protects against bile acid-mediated cholestatic liver injury in mice," Presented at the EASL Conference, London, UK, Apr. 12, 2015, http://www.albireopharma.com/News.aspx?PageID=1591817, 22 pages.
Bajor et al., "Bile acids: short and long term effects in the intestine," Scandanavian J. Gastro., 2010, 45:645-664.
Banker et al., "Modern Pharmaceutics, 3ed", Marcel Dekker, New York, 1996, pp. 451 and 596.
Bavin, "Polymorphism in Process Development," Chemistry and Industry, 527-529, 1989.
Board of Appeal of European Patent Office, Case No. T 077/08-3.3.01, dated May 24, 2011, 17 pages.
Bonge et al., "Cytostar-T Scintillating Microplate Assay for Measurement of Sodium-Dependent Bile Acid Uptake in Transfected HEK-293 Cells," Analytical Biochemistry, 2000, 282:94-101.
Brunzell and Hokanson, "Dislipidemia of Central Obesity and Insulin Resistance," Diabetes Care, 1999, 22(Suppl. 3):C10-C13.
Byrn et al., "Pharmaceutical Solids: A Strategic Approach to Regulatory Considerations," Pharmaceutical Research, 1995, 12(7), pp. 945-954.
Chen et al., "Inhibition of apical sodium-dependent bile acid transporter as a novel treatment for diabetes," Am J Physiol Endocrinol Metab, 2012, 302:E68-E76.
Chen et al., "Progressive Familial Intrahepatic Cholestasis, Type 1, Is Associated with Decreased Farnesoid X Receptor Activity," Gastroenterology, 2004, 126:756-764.
Chey et al., "A Randomized Placebo-Controlled Phase II b Trial of A3309, a Bile Acid Transporter Inhibitor, for Chronic Idiopathic Constipation," Am. J. Gastroenterology, May 2011, 106:1803-1812.
Chourasia et al., "Polysaccharides for colon targeted drug delivery," Drug Delivery, Academic Press, vol. 11, No. 2, Jan. 1, 2004, XP008060983.
Dashti et al., "A Phospholipidomic Analysis of All Defined Human Plasma Lipoproteins," Nature.com: Scientific Reports, Nov. 2011, DOI: 10.1038, 11 pages.
Davit_Spraul et al., "ATP8B1 and ABCB11 Analysis in 62 Children with Normal Gamma-Glutamyl Transferase Progressive Familial Intrahepatic Cholestasis (PFIC): Phenotypic Differences Between PFIC1 and PFIC2 and Natural History," *Hepatology: Autoimmune, Cholestatic and Biliary Disease*, May 2010, 1645-1655.
Davit-Spraul et al., "Progressive familial intrahepatic cholestasis," *Orphanet Journal of Rare Diseases*, Jan. 2009, 4:1-12.
Dawson et al., "Bile acid transporters" J. Lipid Res. 2009, 50, 2340-2357.
DeFronzo et al., "Insuline resistance, a multisurfaced syndrome responsible for NIDDM, obesity, hypertension, dyslipidemia and atherosclerotic cardiovascular disease," Diabetes Care, 1991, 14:173-194.
Di Padova et al., "Double-blind placebo-controlled clinical trial of microporous chlestyramine in the treatment of intra- and extrahepatic cholestasis: relationship between itching and serum bile acids," Methods Find Exp Clin Pharmacol., Dec. 1984, 6(12):773-776 (Abstract Only).
Dongiovanni et al., "Genetic Predisposition in NAFLD and NASH: Impact on Severity of Liver Disease and Response to Treatment," Curren Pharma Design, 2013, 19:5219-5238.
Espenshade and Hughes, "Regulation of Sterol Synthesis in Eukaryotes," Annu. Rev. Genet., 2007, 41:401-427.
Evonik Industries, "Eudragit FS 30 D," Jul. 9, 2008, http://www.pharma-polymers.com.pharmapolymers/MCMbase/Pages/ProvideResource.aspx?respath=/NR/rdonlyres/BDD7E168-922E-4AB1-861F-EEEB58B85642/0/EUDRAGITFS30D_Promotiondatasheet_09072008.
Extended European Search Report in European Application No. 11840392.2, dated Feb. 24, 2014, 7 pages.

(56) References Cited

OTHER PUBLICATIONS

Extended European Search Report in European Application No. 11840481.3, dated Feb. 13, 2014, 10 pages.
Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.
Gillberg et al., "The IBAT Inhibition by A3309—A Potential Mechanism for the Treatment of Constipation," Gastroenterology, 2010, 138(5), Supp 1, S-224.
Glasgov et al., "Compensatory enlargement of human athersclerotic coronary arteries," N Engl. J. Med., May 1987, 316(22):1371-1375 (Abstract Only).
Govers et al., "Characterization of the adsorption of conjugated and unconjugated bile acids to insoluble, amorphous calcium phosphate", Journal of Lipid Research 35(5):741-748, 1994.
Hancock et al., "Molecular Mobility of amorphous pharmaceutical solids below their glass transition temperatures," 12(6): 799-806, 1995.
Heathcote, "Management of primary biliary cirrhosis," Hepatology, 2000, 31(4):1005-1013.
Higaki et al., "Inhibition of ileal na+/bile acid cotranporter by S-8921 reduces serum cholesteral and prevents atherosclerosis in rabbits", Arteriosclerosis, Thrombosis, and Vascular Biology 18(8):1304-1311, 1998.
Huang et al., "Discovery of Potent, Nonsystemic Apical Sodium-Codependent Bile Acid Transporter Inhibitors (Part 2)," J. Med. Chem., 2005, 48:5853-5868.
International Preliminary Report on Patentability for International Application No. PCT/SE2011/051335, dated May 23, 2011, 7 pages.
International Preliminary Report on Patentability for International Application No. PCT/SE2011/051336, dated May 23, 2013, 11 pages.
International Search Report and Written Opinion for Application No. PCT/EP2014/058432, dated Jul. 11, 2014, 9 pages.
International Search Report and Written Opinion for International Application No. PCT/SE2011/051335, dated Feb. 3, 2012, 12pages.
International Search Report and Written Opinion for International Application No. PCT/SE2011/051336, dated Feb. 22, 2012, 18 pages.
Ishibashi et al., "Hypercholesterolemia in low density lipoprotein receptor knockout mice and its reversal by adenovirus-mediated gene delivery", Journal of Clinical Investigation 92(2):883-893, 1993.
Jacquet et al., "Alagille Syndrome in Adult Patients: It is Never Too Late," *American Journal of Kidney Diseases*, May 2007, 49(5):705-709.
Korman et al., "Assessment of Activity in Chronic Active Liver Disease," New England Journal of Medicine, 2010, 290(25):1399-1402.
Kumar and Tandon, "Use of ursodeoxycholic acid in liver diseases," J. Gastroenterology and Hepatology, 2001, 16:3-14.
Kurata et al., "A novel class of apical sodium-dependent bile acid transporter inhibitors: the amphiphilic 4-oxo-1-phenyl-1,4-dihydroquinoline derivatives," Bioorganic & Medicinal Chemistry Letters, 2004, 14:1183-1186.
Lanzini et al., "Intestinal absorption of the bile acid analogue $^{75}$Se-homocholic acid-taurine is increased in primary biliary cirrhosis and reverts to normal during ursodeoycholic acid administrations," Gut, 2003, 52:1371-1375.
Lewis et al., "Effects of 2164U90 on ileal bile acid adsorption and serum cholesterol in rats and mice", Journal of Lipid Research 36(5):1098-1105, 1995.
Ling, "Congenital cholestatic syndromes: What happens when children grow up?," Can J Gastroenterol, Nov. 11, 2007, 21(11):743-751.
Longo et al., "Hyperlipidemia in chronic cholestatic liver disease," Curr. Treat. Options Gastrenterol., 2001, 4:111-114.
Lykavieris et al., "Outcome of liver disease in children with Alagille syndrome: a study of 163 patients," Gut, 2001, 49:431-435.
MerckManuals.com', "Obesity," 2008, Merch Manual for Health Care Professionals, Section-Nutritional Disorders, Chapter— "Obesity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.
Morissette et al., "High-throughput crystallization: polymorphs, salts, co-crystals and solvates of pharmaceutical solids," Advanced Drug Delivery Reviews, 2004, 56:275-300.
Nagase et al., "Preparation of Benzothiazepine derivatives with activity of brining about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.
Parker et al., "Molecular mechanisms underlying bile acid-stimulated glucagon-like peptide-1 secretion," British J. Pharmacology, 2012, 165:414-423.
Patani et al., "Bioisosterism: A Rational Approach in Drug Design," Chem Rev, 1996, 96:3147-3176.
Plump et al., "Severe hypercholesterolemia and atherosclerosis in apolipoprotein E-deficient mice created by homologous recombination in ES cells", Cell (71):343-353, 1992.
Podesta et al., "Treatment of pruritus of primary biliary cirrhosis with rifampin," Dig. Dis. Sci, 1991, 36(2):216-220.
Poupon et al., "Chronic Cholestatic Disease," J. Hepatology, 2000, 32(1):12-140.
Report filed at oral proceedings before opposition division, GMS-CFEP-2007-20, "Filtration and Drying Study on Amorphous and Form IV Atorvastatin Calcium," 2007.
Report EC20082069.02.01 dated Feb. 2009, filed with appellant's letter of Apr. 26, 2011.
Schiller, "Review article: the therapy of constipation", Alimentary Pharmacology and Therapeutics 15(6):749-763, 2001.
Shah et al., "Role of Caco-2 Cell Monolayers in Prediction of Intestinal Drug Absortption," Biotechnol. Prog., 2006, 22:186-198.
Shang et al., "Colesevelam improves insulin resistance in a diet-induced obesity (F-DIO) rat model by increasing the release of GLP-1," Am J. Physiol Gastrointest Liver Physiol, 2010, 298:G419-G424.
Sorrentino et al., "A Clinical-Morphological Study on Cholestatic Presentation of Nonalcoholic Fatty Liver Disease," Digestive Disease and Sciences, Jun. 2005, 50(6):1130-1135.
Sprong et al., "Dietary Calcium Phosphate Promotes Listeria monosytogenes colonization and translocation in rats red diets containing corn oil but not milk fat1", J. Nutrition (US) 132(6):1269-1274, 2002.
Staels and Kuipers, "Bile Acid Sequestrants and the Treatment of Type 2 Diabetes Mellitus," Drugs, 2007, 67(10):1383-1392.
Stein, "Managing Dyslipidemia in the High-Risk Patient," Am J. Cardiol., 2002, 89:50-57.
Tanaka et al., "Genetic and Familial considerations of Primary Biliary Cirrhosis," Am. J. Gastroenterology, 2001, 96(1): 8-15.
Tollefson et al., "A novel class of apical sodium co-dependent bile acid transporter inhibitors: the 1,2-Benzothiazepines", Bioorganic and Medicinal Chemistry Letters 12:3727-3730, 2003.
Tremont et al., "Discovery of Potent, Nonsystemic Apical Sodium-Codependent Bile Acid Transporter Inhibitors (Part 1)," J. Med. Chem, 2005, 48:5837-5852.
Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.
Van Tilberg et al., "Na+-dependent bile acid transport in the ileum: the balance between diarrhea and constipation", Gastroenterology 98(1):25-32, 1989.
Vippagunta et al., "Crystalline solids", Advanced Drug Delivery Reviews 48:3-26, 2001.
Watts and Illum, "Colonic Drug Delivery," Drug Development and Industrial Pharmacy, 1997, 23(9):893-913.
Welberg et al., "Calcium and the prevention of colon cancer", Scandinavian J. Gasteroenterology Suppl. 188:52-59, 1991.

(56) References Cited

OTHER PUBLICATIONS

Williams et al., Foye's Principles of Medicinal Chemistry, 5th Edition, 2002, 59-63.
Wolff, "Burger's Medicinal Chemistry, 5ed, Part I", John Wiley & Sons, 1995, pp. 975-977.
Das & Kar., Non alcoholic steatohepatitis. JAPI. 53:, Mar. 2005.
Berazs et al., Nor-ursodeoxycholic acid reverses hepatocyte-specific nemo-dependnt steatohepatitis. Gut, 2011: 60: 387-396.
Carulli et al, "Review article: effect of bile salt pool composition on hepatic and biliary functions," Aliment. Pharmacol. Ther. 2000, vol. 14, suppl. 2, p. 14-18.
Islam and Di Baise, "Bile Acids: An underrecognized and underappreciated cause of chronic diarrhea," Pract. Gastroenterol. 2012, vol. 36(10), p. 32-44.
Jacobsen et al., "Effect of enterocoated cholestyramine on bowel habit after ileal resection: a double blind crossover study," Br. Med. J. 1985, vol. 290, p. 1315-1318.
Marzorati et al, "A novel hypromellose capsule, with acid resistance properties, permits the targeted delivery of acid-sensitive products to the intestine," LWT-Food Sci. Techno.1 2015, vol. 60, p. 544-551.
Pattni and Walters, "Recent advances in the understanding of bile acid malabsorption," Br. Med. Bull. 2009, vol. 92, p. 79-93.
Possemiers et al, "PCR-DGGE-based quantification of stability of the microbial community in a simulator of the human intestinal microbial ecosystem," FEMS Microbiol. Ecol. 2004, vol. 49, p. 495-507.
Sinha and Kumria, "Microbially triggered drug delivery to the colon," Eur. J. Pharm. Sci. 2003, vol. 18, p. 3-18.
Vertommen and Kinget, "The influence of five selected processing and formulation variables on the particle size, particle size distribution, and friability of pellets produced in a rotary processor," Drug Dev. Ind. Pharm. 1997, vol. 23, p. 39-46.
International Search Report and Written Opinion for Application No. PCT/SE2017/050128, dated May 8, 2017, 16 pages.
International Search Report and Written Opinion for Application No. PCT/SE2017/050126, dated Apr. 24, 2017, 27 pages.
Okubo et al., "II, Daihyoteki Shikkan no Shinryo to Genkyo to Shorai Tenbo 6. Nanjisei Benpi," The Journal of the Japanese Society of Internal Medicine Jan. 10, 2013 (Jan. 10, 2013), 102(1), pp. 83-89.
International Search Report, Application No. PCT/JP2015/068240, dated Sep. 15, 2015.
Alonso et al., "Histologic pathology of the liver in progressive familial intrahepatic cholestasis," Journal of Pediatric Gastroenterology and Nutrition, 14: 128-133, 1994.
Billington et al., "Effects of bile salts on the plasma membranes of isolated rat hepatocytes," Bichem. J. 188: 321-327, 1980.
Bull et al., "Genetic and morphological findings in progressive familial intrahepatic cholestasis (Byler disease [PFIC-1] and Byler syndrome): Evidence for Heterogeneity," Hepatology, 26: 1, 155-164, 1997.
Chen et al., "Bile salt export pump is dysregulated with altered farnesoid X receptor isoform expression in patients with hepatocelular carcinoma," Hepatologu, 57: 4, 1530-1541, 2013.
Chen et al., "Serum and urine metabolite profiling reveals potential biomarkers of human hepatocellular carcinoma," Molecular and Cellular Proteomics 10.7, 2011.
Faubion et al., "Toxic bile salts induce rodent hepatocyte apoptosis via direct activation of Fas," The Journal of Clinical Investigation, 103: 1, 137-145, 1999.
Jansen et al., "Endogenous bile acids as carcinogens," Journal of Hepatology, 47, 434-435, 2007.
Knisely et al., "Hepatocellular Carcinoma in ten children under five years of age with bile salt export pump deficiency," Hepatology, 44: 2, 478-486, 2006.
Kurbegov et al., Biliary diversion for progressive familial intrahepatic cholestasis: Improved liver morphology and bile acid profile, Gastroenterology, 125: 4, 1227-1234, 2003.
Perez et al., "Bile-acid-induced cell injury and protection," World J Gastroenterol, 15: 25, 1677-1689, 2009.
Qiu et al., "Disruption of BSEP function in HepaRG cells alters bile acid disposition and is a susceptive factor to drug-induced cholestatic injury," Mol. Pharmaceutics, 13:4,, 2016 (Abstract only).
Rolo et al., "Bile acids affect liver mitochondrial bioenergetics: Possible relevance for cholestasis therapy," Toxocological Sciences, 57: 177-185, 2000.
Wang et al., "Bile acid receptors and liver cancer," Curr. Pathobiol Rep, 1, 29-35, 2013.
Whitington et al., "Partial external diversion of bile for the treatment of intractable pruitus associated with intrahepatic cholestasis," Gastroenterology, 95: 1, 130-136, 1988 (Abstract only).
Woolbright et al., "Novel insight into mechanisms of cholestatic liver injury," World Journal of Gastroenterology, 18: 36, 4985-4993, 2012.
Yang et al., "Partial external biliary diversion in children with progressive familial intrahepatic cholestasis and alagille disease," Journal of Pediatric Gastroenterology and Nutrition, 49: 216-221, 2009.
Yerushalmi et al., "Bile acid-induced rat hepatocyte apoptosis is inhibited by antioxidants and blockers of the mitochondrial," Hepatology, 33: 3, 616-626, 2001.
Zhang et al., Abcb11 deficiency induces cholestasis coupled to impaired B-Fatty acid oxidation in mice, Journal of biological chemistry, 287: 29, 24784-2479, 2012.
Zhang et al., "Effect of bile duct ligation on bile acid composition in mouse serum and liver," Liver int, 32: 1, 58-69, 2012.
U.S. Appl. No. 15/519,808, filed Apr. 17, 2017, Ymen et al.
U.S. Appl. No. 15/320,651, filed Dec. 20, 2016, Ando et al.
U.S. Appl. No. 13/881,435, filed May 22, 2013, Gillberg et al.
U.S. Appl. No. 14/505,811, filed Oct. 3, 2014, Gillberg et al.
U.S. Appl. No. 13/881,447, filed May 17, 2013, Gillberg et al.
U.S. Appl. No. 14/505,782, filed Oct. 3, 2014, Gillberg et al.
U.S. Appl. No. 15/069,355, filed Mar. 14, 2016, Gillberg et al.
U.S. Appl. No. 15/069,199, filed Mar. 14, 2016, Gillberg et al.
U.S. Appl. No. 15/276,446, filed Sep. 26, 2016, Gillberg et al.
U.S. Appl. No. 15/134,583, filed Apr. 21, 2016, Bohlin et al.
U.S. Appl. No. 15/134,586, filed Apr. 21, 2016, Bohlin et al.
U.S. Appl. No. 15/449,645, filed Mar. 3, 2017, Gillberg et al.
U.S. Appl. No. 15/449,781, filed Mar. 3, 2017, Gillberg et al.
U.S. Appl. No. 15/449,779, filed Mar. 3, 2017, Gillberg et al.
McCullough et al., "The epidemiology and risk factors of NASH.", Blackwell Publishing, Chapter 3, 2005.
Adams et al., "Hepascore: an accurate validated predictor of liver fibrosis in chronic hepatitis C infection," Clin. Chem. 2005, vol. 51(10), p. 1867-1873.
Alashkar et al., "Meeting Info.: 57th Annual Meeting of the AmericanSociety-of-Hematology," Orlando, FL, USA. Dec. 5-8, 2015, Amer Soc Hematol, Blood, 2015, 126(23).
Allison et al., "Studies on mixed populations of human intestinal bacteria grown in single-stage and multistage continuous culture systems," Appl. Environ. Microbial. 1989, 55(3):672-678.
Alvarez et al., "Reduced hepatic expression of farnesoid X receptor in hereditary cholestasis associated to mutation in ATP8B1," Hum Mol Genet, 2004, 13(20):2451-2460.
Angulo et al., "The NAFLD fibrosis score: a noninvasive system that identifies liver fibrosis in patients with NAFLD," Hepatology, 2007, vol. 45(4), p. 846-854.
Anzivino et al., "ABCB4 and ABCB11 mutations in intrahepatic cholestasis of pregnancy in an Italian population," Dig Liver Dis., 2013, 45(3):226-232.
Appleby et al., "Effects of conventional and a novel colonic-release bile acid sequestrant, A3384, on fibroblast growth factor 19 and bile acid metabolism in healthy volunteers and patients with bile acid diarrhoea", United Eur. Gastroent. J., vol. 5, pp. 380-388, 2017.
Arnell et al., "Follow-up in children with progressive familial intrahepatic cholestasis after partial external biliary diversion," J Pediatr Gastroenterol Nutr., 2010, 51(4):494-499.
Beausejour et al., "Description of two new ABCB11 mutations responsible for type 2 benign recurrent intrahepatic cholestasis in a French-Canadian family," Can J Gastroenterol., 2011, 25(6):311-314.

(56) References Cited

OTHER PUBLICATIONS

Bhaskaran et al., "Extrusion Spheronization—A Review," International Journal of PharnnTech Research. vol. 2, No. 4, pp. 2429-2433, Oct.-Dec. 2010 (Year: 2010).
Blackmore et al., "Polymorphisms in ABCB11 and ATP8B1 Associated with Development of Severe Intrahepatic Cholestasis in Hodgkin's Lymphoma," J Clin Exp Hepatol., 2013, 3(2):159-161.
Bounford. University of Birmingham Dissertation Abstracts International, (2016) vol. 75, No. 1C. Order No. AA110588329. ProQuest Dissertations & Theses.
Burrows, "Interventions for treating cholestasis in pregnancy," Cochrane Database Syst. Rev., 4:CD00493, 2001.
Byrne et al., "Missense mutations and single nucleotide polymorphisms in ABCB11 impair bile salt export pump processing and function or disrupt pre-messenger RNA splicing," Hepatology., 2009, 49(2):553-567.
Camilleri, "Probiotics and irritable bowel syndrome: rationale, putative mechanisms, and evidence of clinical efficacy," Clin. Gastroenterol., 40(3):264-9, Mar. 2006.
Centeno, "Molecular mechanisms triggered by low-calcium diets," Nutrition research reviews., 22(2):163-74, Dec. 2009.
Chalasani et al., "The diagnosis and management of nonalcoholic fatty liver disease: Practice guidance from the American Association for the Study of Liver Diseases," Hepatology, 2018, 67(1):328-357.
Chen et al., "Diagnosis of BSEP/ABCB11 mutations in Asian patients with cholestasis using denaturing high performance liquid chromatography," J Pediatr., 2008, 153(6):825-832.
Chen et al., "FIC1 and BSEP defects in Taiwanese patients with chronic intrahepatic cholestasis with low gamma-glutamyltranspeptidase levels," Journal of Pediatrics, 2002, 140(1):119-124.
Chen et al., "The effects of diets enriched in beta-glucans on blood lipoprotein concentrations," J. Clin. Lipidol., 3(3):154-8, May 2009.
Chen et al., "Treatment effect of rifampicin on cholestasis," Internet Journal of Pharmacology, 4(2), 2006.
Chiang, "Bile acids: regulation of synthesis," J. Lipid Res, 2009, 50(10):1955-1966.
Copeland et al., "Novel splice-site mutation in ATP8B1 results in atypical progressive familial intrahepatic cholestasis type 1," J Gastroenterol Hepatol., 2013, 28(3):560-564.
Danese et al., "Analytical evaluation of three enzymatic assays for measuring total bile acids in plasma using a fully-automated clinical chemistry platform," PLoS One, 2017, 12(6):e0179200.
Davit-Spraul et al., "Liver transcript analysis reveals aberrant splicing due to silent and intronic variations in the ABCB11 gene," Mol Genet Metab., 2014, 113(3):225-229.
Dawson, "Role of the intestinal bile acid transporters in bile acid and drug disposition," Handb Exp. Pharmacol. 2011, 201:169-203.
De Lédinghen et al., "Controlled attenuation parameter for the diagnosis of steatosis in non-alcoholic fatty liver disease," J Gastroenterol Hepatol., 2016, 31(4):848-855.
Deng et al., "Novel ATP8B1 mutation in an adult male with progressive familial intrahepatic cholestasis," World J Gastroenterol., 2012, 18(44):6504-6509.
Di Lascio et al., "Steato-Score: Non-Invasive Quantitative Assessment of Liver Fat by Ultrasound Imaging," Ultrasound Med Biol., 2018, 44(8):1585-1596.
DiBaise et al., "Bile Acids: An Underrecognized and Underappreciated Cause of Chronic Diarrhea", Pract. Gastroenterol. vol. 36(10), p. 32-44, 2012.
Dixon et al., "An expanded role for heterozygous mutations of ABCB4, ABCB11, ATP8B1, ABCC2 and TJP2 in intrahepatic cholestasis of pregnancy," Scientific Reports, 2017, 7(1):11823.
Dong et al., "Structure-activity relationship for FDA approved drugs as inhibitors of the human sodium taurocholate cotransporting polypeptide (NTCP).," Mol. Pharm. 2013, 10(3):1008-1019.
Drage et al., "Exon-skipping and mRNA decay in human liver tissue: molecular consequences of pathogenic bile salt export pump mutations," Sci Rep., 2016, vol. 6: 24827.
Drage et al., "Sequencing of FIC1, BSEP and MDR3 in a large cohort of patients with cholestasis revealed a high number different genetic variants," J Hepatol. 2017, 67(6):1253-1264.
Droge et al., Zeitschrift fur Gastroenterologie 2015, 53(12) Abstract No. A3-27. Meeting Info: 32. Jahrestagung der Deutschen Arbeitsgemeinschaft zum Studium der Leber. Dusseldorf, Germany. Jan. 22, 2016-Jan. 23, 2016.
Drumond et al., "Patients' appropriateness, acceptability, usability and preferences for pharmaceutical preparations: Results from a literature review on clinical evidence," Int. J. Pharm. 2017, 521(1-2):294-305.
Einspahr et al., "Protective role of wheat bran fiber: data from marker trials," Am. J. Med., 106(1A):32s-37s, Jan. 1999.
Ellinger et al., "Partial external biliary diversion in bile salt export pump deficiency: Association between outcome and mutation," World J Gastroenterol., 2017, 23(29):5295-5303.
Ellis et al., "Zebrafish abcb11b mutant reveals strategies to restore bile excretion impaired by bile salt export pump deficiency," Hepatology, 2018, 67(4)1531-1545.
Engelen et al., "Oral size perception of particles: effect of size, type, viscosity and method," J. Text. Studies 2005, 36(4):373-386.
Evason et al., "Morphologic findings in progressive familial intrahepatic cholestasis 2 (PFIC2): correlation with genetic and immunohistochemical studies," Am J Surg Pathol., 2011, 35(5):687-696.
Ferreira et al., Pediatric Transplantation 2013, 17(SUPPL. 1):99. Abstract No. 239. Meeting Info: IPTA 7th Congress on Pediatric Transplantation. Warsaw, Poland. Jul. 13, 2013-Jul. 16, 2013.
Ferslew et al., "Altered Bile Acid Metabolome in Patients with Nonalcoholic Steatohepatitis," Dig Dis Sci., 2015, 60(11):3318-3328.
Folmer et al., "Differential effects of progressive familial intrahepatic cholestasis type 1 and benign recurrent intrahepatic cholestasis type 1 mutations on canalicular localization of ATP8B1," Hepatology., 2009, 50(5):1597-1605.
Francalanci et al., "Progressive familial intrahepatic cholestasis: Detection of new mutations and unusal modality of transmission," Digestive and Liver Disease 2010, 42(SUPPL. 1):516, Abstract No. T.N.5.
Francalanci et al., Laboratory Investigation 2011, vol. 91, Supp. SUPPL. 1, pp. 360A. Abstract No. 1526.
Fuentes-Zaragoza al., "Resistant Starch as functional ingredient: A review", Food Research International, 43, 931-942, 2010.
Fuller, "Probiotics in man and animals," Appl. Bacterial. 1989, 66(5):365-378.
Gao et al., "Detection of hepatitis in children with idiopathic cholestatic bile salt export pump gene mutations," Shandong Yiyao, 2012, 52(10):14-16.
Gao et al., "The Identification of Two New ABCB11 Gene Mutations and the Treatment Outcome in a Young Adult with Benign Recurrent Intrahepatic Cholestasis: A Case Report," Hepatitis Monthly 2017, 17(10):e55087/1-e55087/6.
Gibson and Roberfroid, "Dietary modulation of the human colonic microbiota: introducing the concept of prebiotics," J. Nutr. 1995, 125(6):1401-1412.
Giovannoni et al., "Genetics and Molecular Modeling of New Mutations of Familial Intrahepatic Cholestasis in a Single Italian Center," PLoS One, 2015, 10(12):e0145021.
Goldschmidt et al., "Increased frequency of double and triple heterozygous gene variants in children with intrahepatic cholestasis," Hepatol Res., 2016, 46(4):306-311.
Griffin, et al., "A novel gene mutation in ABCB11 in siblings with progessive familial intrahepatic cholestasis type 2," Canadian Journal of Gastroenterology and Hepatology 2016, vol. 2016. Abstract No. A200. Meeting Info: 2016 Canadian Digestive Diseases Week, CDDW 2016. Montreal, QC, United States. Feb. 26, 2016-Feb. 29, 2016.
Gunaydin et al., "Progressive familial intrahepatic cholestasis: diagnosis, management, and treatment," Hepat Med., 2018, 10:95-104.
Guorui et al., "Genetic diagnosis of progressive familial intrahepatic cholestasis type 2," Linchuang Erke Zazhi, 2013, 31(10):905-909.
Hao et al., "Application of high-throughput sequencing technologies with target capture/target next-generation sequencing in diag-

(56) References Cited

OTHER PUBLICATIONS nosis of neonatal intrahepatic cholestasis causes by citrin deficiency (NICDD)," International Journal of Clinical and Experimental Pathology, 2017, 10(3):3480-3487.

Harmanci et al., "Late onset drug induced cholestasis in a living-related liver transplantation donor to son with progressive familial intrahepatic cholestasis," Experimental and Clinical Transplantation 2015, 13(2):76, Abstract No. P62. Meeting Info: 1st Congress of the Turkic World Transplantation Society. Astana, Kazakhstan. May 20, 2015-May 22, 2015.

Hasegawa et al., "Intractable itch relieved by 4-phenylbutyrate therapy in patients with progressive familial intrahepatic cholestasis type 1," Orphanet J Rare Dis., 2014, 9:89.

Hayashi et al., "Assessment of ATP8B1 Deficiency in Pediatric Patients With Cholestasis Using Peripheral Blood Monocyte-Derived Macrophages," EBioMedicine, 2018, 27:187-199.

Hayashi et al., "Successful treatment with 4-phenylbutyrate in a patient with benign recurrent intrahepatic cholestasis type 2 refractory to biliary drainage and bilirubin absorption," Hepatol Res., 2016, 46(2):192-200.

Herbst et al., "Taking the next step forward—Diagnosing inherited infantile cholestatic disorders with next generation sequencing," Mol Cell Probes, 2015, 29(5):291-298.

Ho et al., "Polymorphic variants in the human bile salt export pump (BSEP; ABCB11): functional characterization and interindividual variability," Pharmacogenet Genomics, 2010, 20(1):45-57.

Hoffman et al., Human Anatomy, picture of the colon, p. 1-7, https://www.webmd.com/digestive-disorders/picture-of-the-colon#1, Accesses Aug. 4, 2019.

Holz et al., "Can genetic testing guide the therapy of cholestatic pruritus? A case of benign recurrent intrahepatic cholestasis type 2 with severe nasobiliary drainage-refractory itch," Hepatol Commun., 2018, 2(2):152-154.

Holz et al., "Plasma separation and anion adsorption results in rapid improvement of nasobiliary drainage (NBD)—refractory pruritus in BRIC type 2," Zeitschrift fur Gastroenterologie 2016, vol. 54, No. 8. Abstract No. KV275. Meeting Info: Viszeralmedizin 2016, 71. Jahrestagung der Deutschen Gesellschaft fur Gastroenterologie, Verdauungs- und Stoffwechselkrankheiten mit Sektion Endoskopie-10. Herbsttagung derDeutschen Gesellschaft fur Allgemein- und Viszeralchirurgie. Hamburg, Germany. Sep. 21, 2016-Sep. 24, 2016

Hsu et al., "Adult progressive intrahepatic cholestasis associated with genetic variations in ATP8B1 and ABCB11," Hepatol Res., 2009, 39(6):625-631.

Hu et al., "Diagnosis of ABCB11 gene mutations in children with intrahepatic cholestasis using high resolution melting analysis and direct sequencing," Mol Med Rep., 2014, 10(3):1264-1274.

Imagawa et al., "Clinical phenotype and molecular analysis of a homozygous ABCB11 mutation responsible for progressive infantile cholestasis," J Hum Genet. 2018, 63(5):569-577.

Imagawa et al., "Generation of a bile salt export pump deficiency model using patient-specific induced pluripotent stem cell-derived hepatocyte-like cells," Sci Rep., 2017, 7:41806.

Imagawa et al., "Splicing analysis using induced pluripotent stem cell-derived hepatocyte-like cells generated from a patient with progressive familial intrahepatic cholestatsis type 2," Journal of Pediatric Gastroenterology and Nutrition 2016, 63(2):551, Abstract No. 166, Meeting Info: World Congress of Pediatric Gastroenterology, Hepatology and Nutrition 2016. Montreal, QC, Canada. Oct. 5, 2016-Oct. 8, 2016

International Search Report and Written Opinion for Appln. No. PCT/EP2019/064602, dated Aug. 9, 2019, 11 pages.

International Search Report and Written Opinion in International Application No. PCT/SE2018/050802, dated Oct. 26, 2018.

International Search Report and Written Opinion in International Application No. PCT/SE2018/050803, dated Oct. 26, 2018.

Ishak et al., "Histological grading and staging of chronic hepatitis," J. Hepatol. 1995, vol. 22, p. 696-699.

Ivashkin et al., "A novel mutation of ATP8B1 gene in young patient with familial intrahepatic cholestasis.," Hepatology International 2016, 10(1):5461, Abstract No. LBO-38. Meeting Info: 25th Annual Conference of the Asian Pacific Association for the Study of the Liver, APASL 2016. Tokyo, Japan. Feb. 20, 2016-Feb. 24, 2016

Jankowska et al., "[Cholestatic liver disease in children]," Przegl. Epidemiol., 56:16-21, 2002.

Jankowska et al., "Ileal exclusion in children with progressive familial intrahepatic cholestasis," J Pediatr Gastroenterol Nutr. 2014,58(1):92-95

Jaquotot-Haerranz et al., "Clinical variability of mutations in the ABCB11 gene: a case report," Rev Esp Enferm Dig., 2013, 105(1):52-54.

Jericho et al., "Bile Acid Pool Dynamics in Progressive Familial Intrahepatic Cholestasis with Partial External Bile Diversion," Journal of Pediatric Gastroenterology and Nutrition, 2015, 60(3):368-374.

Jirsa et al., "Indel in the FIC1/ATP8B1 gene—a novel rare type of mutation associated with benign recurrent intrahepatic cholestasis," Hepatol Res. 2004, 30(1):1-3.

Jung et al., "Prenatal molecular diagnosis of inherited cholestatic diseases," J Pediatr Gastroenterol Nutr. 2007, 44(4):453-458.

Kagawa et al., "Phenotypic differences in PFIC2 and BRIC2 correlate with protein stability of mutant Bsep and impaired taurocholate secretion in MDCK II cells," Am J Physiol Gastrointest Liver Physiol., 2008, 294(1):G58-67.

Kang et al., "Progressive Familial Intrahepatic Cholestasis in Korea: A Clinicopathological Study of Five Patients," J Pathol Transl Med. May 16, 2019, 53(4):253-260.

Karpen and Dawson, "Not all (bile acids) who wander are lost: the first report of a patient with an isolated NTCP defect," Hepatology, 2015, 61(1):24-27.

Khosla et al., "Recurrent Post-partum Jaundice: Rare Genetic Disorder With Novel Genetic Mutations Identified," American Journal of Gastroenterology 2015, 110(1):5397. Meeting Info.: 80th Annual Scientific Meeting of the American-College-of-Gastroenterology. Honolulu, HI, USA. Oct. 16-21, 2015.

Kim, "Novel mutation of ABCB11 heterozygote associated with transient neonatal intrahepatic cholestasis," Journal of Pediatric Gastroenterology and Nutrition 2016, 62(1):620, Abstract No. H-P-045. Meeting Info: 49th Annual Meeting of the European Society for Pediatric Gastroenterology, Hepatology and Nutrition, ESPGHAN 2016. Athens, Greece. May 25, 2016-May 28, 2016.

Kleiner et al., "Design and validation of a histological scoring system for nonalcoholic fatty liver disease," Hepatology, 2005, 41(6):1313-1321.

Klomp et al., "Characterization of mutations in ATP8B1 associated with hereditary cholestasis," Hepatology, 2004, 40(1):27-38.

Kooistra, et al., "KLIFS: A structural kinase-ligand interaction database," Nucleic Acids Res. 2016, 44(D1):D365-D371.

Kooistra, et al., "KLIFS: A structural kinase-ligand interaction database," Nucleic Acids Res., 2016, vol. 44, No. D1, pp. D365-D371.

Kosters et al., "Bile acid transporters in health and disease," Xenobiotica 2008, 38(7-8):1043-1071.

Kozarewicz, "Regulatory perspectives on acceptability testing of dosage forms in children," Int. J. Pharm. 2014, 469(2):245-248.

Krawczyk et al., "Prolonged cholestasis triggered by hepatitis A virus infection and variants of the hepatocanalicular phospholipid and bile salt transporters," Ann Hepatol., 2012, 11(5):710-744.

Lam et al., "A patient with novel ABCB11 gene mutations with phenotypic transition between BRIC2 and PFIC2," J Hepatol. 2006, 44(1):240-242.

Lam et al., "Levels of plasma membrane expression in progressive and benign mutations of the bile salt export pump (Bsep/Abcb11) correlate with severity of cholestatic diseases," Am J Physiol Cell Physiol. 2007, 293(5):C1709-16.

Lang et al., "Genetic variability, haplotype structures, and ethnic diversity of hepatic transporters MDR3 (ABCB4) and bile salt export pump (ABCB11)," Drug Metab Dispos. 2006, 34(9):1582-1599.

Lang et al., "Mutations and polymorphisms in the bile salt export pump and the multidrug resistance protein 3 associated with drug-induced liver injury," Pharmacogenet Genomics, 2007, 17(1):47-60.

(56) References Cited

OTHER PUBLICATIONS

Lee et al., "Early Diagnosis of ABCB11 Spectrum Liver Disorders by Next Generation Sequencing," Pediatr Gastroenterol Hepatol Nutr. 2017, 20(2):114-123.

Li et al., "ATPSB1 and ABCB11 mutations in Chinese patients with normal gamma-glutamyl transferase cholestasis: Phenotypic differences between progressive familial intrahepatic cholestasis type 1 and 2," Hepatology International 2017, 11(1):5180. Abstract No. OP284

Li et al., "Clinical feature and gene mutation analysis of one pedigree with progressive familial intrahepatic cholestasis type II," Hepatology International 2017, 11(1):5362, Abstract No. PP0347. Meeting Info: 26th Annual Conference of the Asian Pacific Association for the Study of the Liver, APASL 2017. Shanghai, China Feb. 15, 2017-Feb. 19, 2017.

Li et al., "Effect of Resistant Starch Film Properties on the Colon-Targeting Release of Drug From Coated Pellets", 152 J Control. Rel. e5, 2011.

Lichtinghagen R, et al., "The Enhanced Liver Fibrosis (ELF) score: normal values, influence factors and proposed cut-off values," J Hepatol. Aug. 2013;59(2):236-42.

Lin et al., "[Clinical and genetic analysis of an infant with progressive familial intrahepatic cholestasis type II].," Zhongguo Dang Dai Er Ke Za Zhi. 2018, 20(9)758-764 (with English abstract).

Liu et al., "ABCB11 gene mutations in Chinese children with progressive intrahepatic cholestasis and low gamma glutamyltransferase," Liver International 2010, 30(6):809-815.

Liu et al., "Association of variants of ABCB11 with transient neonatal cholestasis," Pediatr Int. 2013, 55(2):138-144.

Liu et al., "Characterization of ATP8B1 gene mutations and a hot-linked mutation found in Chinese children with progressive intrahepatic cholestasis and low GGT," J Pediatr Gastroenterol Nutr., 2010, 50(2):179-183.

Liu et al., "Characterization of ATP8B1 mutations and a hot linked mutation found in Chinese children with progressive intrahepatic cholestasis and low GGT," Hepatology International 2009, 3(1):184-185, Abstract No. PE405. Meeting Info: 19th Conference of the Asian Pacific Association for the Study of the Liver. Hong Kong, China. Feb. 13, 2009-Feb. 16, 2009.

Liu et al., "Homozygous p.Ser267Phe in SLC10A1 is associated with a new type of hypercholanemia and implications for personalized medicine," Scientific Reports, 2017, 7:9214.

Liu, et al "Patient-centered pharmaceutical design to improve acceptability of medicines: similarities and differences in paediatric and geriatric populations," Drugs 2014, 74(16):1871-1889.

Lopez et al., "Effect of formulation variables on oral grittiness and preferences of multiparticulate formulations in adult volunteers," Eur. J. Pharm. Sci. 2016, 92:156-162.

Lv et al., "Noninvasive Quantitative Detection Methods of Liver Fat Content in Nonalcoholic Fatty Liver Disease," J Clin Transl Hepatol. 2018, 6(2):217-221.

Maggiore et al., "Relapsing features of bile salt export pump deficiency after liver transplantation in two patients with progressive familial intrahepatic cholestasis type 2," J Hepatol. 2010, 53(5):981-6.

Manghat and Wierzbicki, "Colesevelam hydrochloride: a specifically engineered bile acid sequestrant," Future Lipidology, 3(3):237-255, Jun. 2008.

Masahata et al., "Recurrence of Progressive Familial Intrahepatic Cholestasis Type 2 Phenotype After Living-donor Liver Transplantation: A Case Report," Transplant Proc. 2016, 48(9):3156-3162.

Matte et al., "Analysis of gene mutations in children with cholestasis of undefined etiology," J Pediatr Gastroenterol Nutr. 2010, 51(4):488-493.

McKay et al., "Mutation detection in cholestatic patients using microarray resequencing of ATP8B1 and ABCB11 [version 2; peer review: 2 approved, 1 approved with reservations]," F1000 Res., 2013, 2:32.

McMichael and Potter, "Reproduction, endogenous and exogenous sex hormones, and colon cancer: a review and hypothesis," J. Natl. Cancer Inst., 65(6):1201-07, Dec. 1980.

McPherson et al., "Simple non-invasive fibrosis scoring systems can reliably exclude advanced fibrosisin. patients with non-alcoholic fatty liver disease," Gut 2010, 59(9):1265-9.

Miloh et al., Gastroenterology 2006, vol. 130, No. 4, Suppl. 2, pp. A759-A760. Meeting Info.: Digestive Disease Week Meeting/107th Annual Meeting of the American-Gastroenterological Association. Los Angeles, CA, USA. May 19.

Minekus et al., "A computer-controlled system to simulate conditions of the large intestine with peristaltic mixing, water absorption and absorption of fermentation products," Appl. Microbiol Biatechnol. 1999, 53(1):108-114.

Mishra et al., "Investigation of organoleptic characteristics in the development of soft chews of calcium carbonate as mineral supplement," Yakugaku Zasshi 2009, 129(12):1537-1544.

Mistry et al., "Evidence of acceptability of oral paediatric medicines: a review," J. Pharm. Pharmacol. 2017, 69(4):361-376.

Mizuochi et al., "Characterization of urinary bile acids in a pediatric BRIC-1 patient: effect of rifampicin treatment," Clin Chim Acta. 2012, 413(15-16):1301-1304.

Moghadamrad et al., "Cholestasis in a patient with gallstones and a normal gamma-glutamyl transferase," Hepatology, 2013, 57(6):2539-2541.

Molly et al., "Development of a 5-step multi-chamber reactor as a simulation of the human intestinal microbial system," Appl. Microbiol. Biatechnol. 1993, 39:254-258.

Mowat et al., "Respiratory chain complex III [correction of complex] in deficiency with pruritus: a novel vitamin responsive clinical feature," J. Pediatr., 134(3):352-4, Mar. 1999.

Nagasaka et al., "Depletion of high-density lipoprotein and appearance of triglyceride-rich low-density lipoprotein in a Japanese patient with FIC1 deficiency manifesting benign recurrent intrahepatic cholestasis," J Pediatr Gastroenterol Nutr., 2007, 45(1)96-105.

Narchi et al., "Intrahepatic cholestasis in two omani siblings associated with a novel homozygous ATP8B1 mutation, c.379C>G (p. L127V).," Saudi J Gastroenterol. 2017, 23(5):303-305.

Neuman, et al., "Biomarkers in nonalcoholic fatty liver disease," Can. J. Gastroenterol. Hepatol. 2014, 28(11):607-618.

Ng et al., "Autoimmune haemolytic anaemia with giant cell hepatitis and concurrent bile salt export pump deficiency: Challenges in diagnosis and management," Journal of Pediatric Gastroenterology and Nutrition 2018, 66(2):860, Abstract No. H-P-127. Meeting Info: 51st Annual Meeting European Society for Paediatric Gastroenterology, Hepatology and Nutrition, ESPGHAN 2018. Geneva, Switzerland. May 9, 2018-May 12, 2018.

Noe et al., "Impaired expression and function of the bile salt export pump due to three novel ABCB11 mutations in intrahepatic cholestasis," J Hepatol. 2005, 43(3):536-543.

O'Neill et al., "Comparison of efficacy of plant stanol ester and sterol ester: short-term and longer-term studies," American Journal of Cardiology, 96(1A):29d-36D, Jul. 2005.

Pai et al. Compression and evaluation of extended release matrix pellets prepared by the extrusion/spheronization process into disintegrating tablets. Brazilian Journal of Pharmaceutical Sciences. vol. 48, n. 1, janinnar., 2012 (Year: 2012).

Painter et al., "Sequence variation in the ATP8B1 gene and intrahepatic cholestasis of pregnancy," Eur J Hum Genet. 2005, 13(4):435-439.

Park et al., "Clinical and ABCB11 profiles in Korean infants with progressive familial intrahepatic cholestasis," World J Gastroenterol., 2016, 22(20):4901-4907.

Pauli-Magnus et al., "Enterohepatic transport of bile salts and genetics of cholestasis," Journal of Hepatology, 2005, 43(2):342-357.

Pauli-Magnus et al., "Impaired expression and function of the bile salt export pump due to three novel ABCB11 mutations in intrahepatic cholestasis," Hepatology 2003, vol. 38, No. 4 Suppl. 1, pp. 518A. print. Meeting Info.: 54th Annual Meeting of the American Association for the Study of Liver Diseases. Boston, MA, USA. Oct. 24-28, 2003. American Association for the Study of Liver Diseases.

(56) References Cited

OTHER PUBLICATIONS

Peng et al., "[Relationship between phenotype and genotype of ABCB11 deficiency in siblings and literature review].," Zhonghua er ke za zhi (Chinese journal of pediatrics) 2018, 56(6):440-444.
Qiu et al., "Defects in myosin VB are associated with a spectrum of previously undiagnosed low γ-glutamyltransferase cholestasis," Hepatology 2017, 65(5)1655-1669.
Reeder et al., "Quantitative assessment of liver fat with magnetic resonance imaging and spectroscopy," J Magn Reson Imaging. 2011, 34(4):729-749.
Renga et al., "Role of FXR in regulating bile acid homeostasis and relevance for human diseases," Curr. Drug. Targets Immune Endocr. Metabol. Disord., 5(3):289-303, Sep. 2005.
Rumbo et al., Transplantation 2018, vol. 102, No. 7, Supp. Supplement 1, pp. 5848. Abstract No. P.752. Meeting Info: 27th International Congress of the Transplantation Society, TTS 2018. Madrid, Spain. Jun. 30, 2018-Jul. 5, 2018.
Sanyal et al. The etiology of hepatocellular carcinonna and consequences of treatment. The Oncologist, 2010, 15 Suppl 4, 14-22.
Sattler et al., "Functional analysis of previously uncharacterized disease-causing mutations of the bile salt export pump," Journal of Hepatology 2017, 66(1):5177. Meeting Info.: International Liver Congress/ 52nd Annual Meeting of the European-Association-for-the-Studyof-the-Liver. Amsterdam, Netherlands. Apr. 19-23, 2017. European Assoc Study Liver.
Scheimann et al., "Prevalence of Abcb 11 mutations among children with cholelithiasis," Gastroenterology 2007, 132(4)Suppl. 2:A452, Meeting Info.: Digestive Disease Week Meeting/108th Annual Meeting of the American-Gastroenterological Association. Washington, DC, USA. May 19-24, 2007. Amer Gastroenterol Assoc; Amer Assoc Study Liver Dis; Amer Soc Gastrointestinal Endoscopy; Soc Surg Alimentary Tract.
Schumpelick et al., "[Ulcerative colitis—late functional results of ileoanal pouch anastomosis]," Chirurg, 69(10):1013-19, Oct. 1998.
Sciveres. "Relapsing features of bile salt export pump (BSEP) deficiency in a patient successfully transplanted for progressive familial intrahepatic cholestasis type 2 (PFIC2).," Digestive and Liver Disease 2010, 42(5):5329. Abstract No. C018. Meeting Info: 17th National Congress SIGENP. Pescara, Italy. Oct. 7, 2010-Oct. 9, 2010.
Shah et al., "Progressive Familial Intrahepatic Cholestasis Type 2 in an Indian Child," J Pediatr Genet. 2017, 6(2):126-127.
Shaprio et al., "DHPLC screening for mutations in progressive familial intrahepatic cholestasis patients," J Hum Genet. 2010, 55(5):308-313.
Sharma et al., "Spectrum of genomic variations in Indian patients with progressive familial intrahepatic cholestasis," BMC Gastroenterol, 2018, 18(1):107.
Sharma et al., "Spectrum of sequence variations in Indian patients with progressive familial intrahepatic cholestasis show several novel polymorphisms," Indian Journal of Gastroenterology 2017, 36(1):A99. Abstract No. M-20. Meeting Info: 58th Annual Conference of the Indian Society of Gastroenterology, ISGCON 2017. Bhubaneswar, India. Dec. 14, 2017-Dec. 17, 2017.
Sherrif et al., "Hepatotoxicity from anabolic androgenic steroids marketed as dietary supplements: contribution from ATP8B1/ABCB11 mutations?," Liver international: official journal of the International Association for the Study of the Liver, 2013, 33(8):1266-1270.
Shimizu et al., "Living-related liver transplantation for siblings with progressive familial intrahepatic cholestasis 2, with novel genetic findings," Am J Transplant. 2011, 11(2):394-398.
Simons, "The fate of the orally administered bile acid sequestrant, polidexide, in humans," Clin. Exp. Pharmacol. Physiol., 3(1):99-101, Jan.-Feb. 1976.
Sirtori, "Mechanisms of lipid-lowering agents," Cardiology, 78(3):226-35, 1991.
Sohn et al., "Benign Recurrent Intrahepatic Cholestasis Type 2 in Siblings with Novel ABCB11 Mutations," Pediatr Gastroenterol Hepatol Nutr. 2019, 22(2):201-206.

Squires et al., "Clinical Variability After Partial External Biliary Diversion in Familial Intrahepatic Cholestasis 1 Deficiency," J Pediatr Gastroenterol Nutr. 2017, 64(3):425-430.
Staels and Kuipers, "Bile acid sequestrants and the treatment of type 2 diabetes mellitus," Drugs, 67(10):1383-92, 2007.
Stindt et al., "A novel mutation within a transmembrane helix of the bile salt export pump (BSEP, ABCB11) with delayed development of cirrhosis," Liver Int. 2013, 33(10):1527-1735.
Stolz et al., "Severe and protracted cholestasis in 44 young men taking bodybuilding supplements: assessment of genetic, clinical and chemical risk factors," Aliment Pharmacol Ther. 2019, 49(9):1195-1204.
Stone et al., "Biochemical characterization of P4-ATPase mutations identified in patients with progressive familial intrahepatic cholestasis," J Biol Chem. 2012, 287(49):41139-51.
Strautnieks et al., "Severe bile salt export pump deficiency: 82 different ABCB11 mutations in 109 families," Gastroenterology. 2008, 134(4):1203-1214.
Suzuki and Takada, "Mechanisms of regulation of bile acid transport in the small intestine," Falk Symposium, 165:76-81, 2009.
Swedish Office Action for Swedish Appln. No. 1850915-8, dated Feb. 15, 2019, 6 pages.
Swedish Search Report for Swedish Appln. No. 1850915-8, dated Feb. 15, 2019, 2 pages.
Takahashi et al., "Gradual improvement of liver function after administration of ursodeoxycholic acid in an infant with a novel ABCB11 gene mutation with phenotypic continuum between BRIC2 and PFIC2," Eur J Gastroenterol Hepatol. 2007, 19(11):942-6.
Tibesar et al., "Two Cases of Progressive Familial Intrahepatic Cholestasis Type 2 Presenting with Severe Coagulopathy without Jaundice," Case Rep Pediatr. 2014, 2014:185923.
Togawa et al., "Diversity of ATP8B1 mutations in japanese patients with intrahepatic cholestasis associated with low gamma-glutamyl transpeptidase level," Journal of Pediatric Gastroenterology and Nutrition 2018, 67(1):5363, Abstract No. 615.
Treepongkaruna et al., "Novel ABCB11 mutations in a Thai infant with progressive familial intrahepatic cholestasis," World J Gastroenterol. 2009, 15(34):4339-4342.
Tyle, "Effect of size, shape and hardness of particles in suspension on oral texture and palatability," Acta Psychologica 1993, 84(1):111-118.
Uegaki et al., "Successful treatment with colestimide for a bout of cholestasis in a Japanese patient with benign recurrent intrahepatic cholestasis caused by ATP8B1 mutation," Intern Med. 2008, 47(7):599-602.
Van der Woerd et al., "Analysis of aberrant pre-messenger RNA splicing resulting from mutations in ATP8B1 and efficient in vitro rescue by adapted U1 small nuclear RNA," Hepatology 2015, 61(4):1382-1391.
Van der Woerd et al., "Mutational analysis of ATP8B1 in patients with chronic pancreatitis," PLoS One. 2013, 8(11):e80553.
Van Mil et al., "Benign recurrent intrahepatic cholestasis type 2 is caused by mutations in ABCB11," Gastroenterology. 2004, 127(2):379-384.
Varma et al., "Retargeting of bile salt export pump and favorable outcome in children with progressive familial intrahepatic cholestasis type 2," Hepatology 2015, 62(1):198-206.
Vaz et al., "Sodium taurocholate cotransporting polypeptide (SLC10A1) deficiency: conjugated hypercholanemia without a clear clinical phenotype," Hepatology, 2015, 61(1):260-267.
Vitale et al., "Cryptogenic cholestasis in young and adults: ATP8B1, ABCB11, ABCB4, and TJP2 gene variants analysis by high-throughput sequencing," J Gastroenterol. 2018, 53(8):945-958.
Waisbourd-Zinman et al., "A Rare BSEP Mutation Associated with a Mild Form of Progressive Familial Intrahepatic Cholestasis Type 2," Ann Hepatol. 2017, 16(3):465-468.
Walkowiak-Tomczak, "Characteristics of plums as a raw material with valuable nutritive and dietary properties—a review," Pol. J. Food Nutr. Sci., 58(4):401-405, 2008.
Walsh et al., "Patient acceptability, safety and access: A balancing act for selecting age-appropriate oral dosage forms for paediatric and geriatric populations," Int. J. Pharm. 2017, 536(2):547-562.

(56) References Cited

OTHER PUBLICATIONS

Wang et al., "Splicing analysis of rare/novel synonymous or intronic variants identified in ABCB11 heterozygotes presenting as progressive intrahepatic cholestasis with low γ-glutamyltransferase," Hepatol Res. 2018, 48(7):574-584.

Wang et al., "The Features of GGT in Patients with ATP8B1 or ABCB11 Deficiency Improve the Diagnostic Efficiency," PLoS One. 2016; 11(4):e0153114.

Wong et al., "Utility of oligonucleotide array-based comparative genomic hybridization for detection of target gene deletions," Clin Chem. 2008, 54(7)1141-1148.

Wu et al., "Discovery of a highly potent, nonabsorbable apical sodium-dependent bile acid transporter inhibitor (GSK2330672) for treatment of type 2 diabetes," J. Med. Chem., 2013, 53(12):5094-5117.

Zarenezhad et al., "Investigation of Common Variations of ABCB4, ATP8B1 and ABCB11 Genes in Patients with Progressive Familial Intrahepatic Cholestasis," Hepatitis Monthly: 2017, 17(2):e43500.

\* cited by examiner

SOLID FORMULATION AND METHOD FOR PREVENTING OR REDUCING COLORATION THEREOF

CROSS-REFERENCE TO RELATED APPLICATIONS

This application is a National Stage application under 35 U.S.C. § 371 of International Application No. PCT/JP2015/068242, filed Jun. 24, 2015, which claims the benefit of JP Application No. 2014-130092, filed on Jun. 25, 2014. The disclosures of the prior applications are hereby incorporated by reference in their entirety.

TECHNICAL FIELD

The present invention relates to prevention or reduction of coloration of a solid formulation containing a benzothia(dia)zepine derivative or a pharmaceutically acceptable salt, solvate, or solvate of such a salt.

BACKGROUND ART

It is known that some benzothia(dia)zepine derivatives function as inhibitors of IBAT (Ileal Bile Acid Transporter) (Patent Document 1). The inhibitors of IBAT are useful in the treatment of dyslipidemic conditions and disorders such as hyperlipidemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL).

In addition, the benzothia(dia)zepine derivatives mentioned above are also useful in the treatment of functional constipation and constipation-dominant irritable bowel syndrome (C-IBS) (Patent Document 2 and Patent Document 3).

PRIOR ART DOCUMENTS

Patent Documents

Patent Document 1: Japanese Patent No. 3665055
Patent Document 2: Japanese Patent No. 4870552
Patent Document 3: Japanese Patent No. 5421326

DISCLOSURE OF INVENTION

Technical Problems

The aforementioned benzothia(dia)zepine derivatives or pharmaceutically acceptable salts, solvates, or solvates of such salts (hereinafter, simply referred to as "benzothia(dia)zepine derivative" in some cases) are stable compounds per se. For example, they are stable over time even under an atmosphere of high temperature and/or high humidity.

However, it has been found that there is a problem in that in the case of blending the aforementioned benzothia(dia)zepine derivative in a solid formulation, the benzothia(dia)zepine derivative may become unstable and coloration of the solid formulation may occur in some cases. In particular, coloration (in particular, red coloration) caused by the aforementioned benzothia (dia)zepine derivative in a solid formulation may occur even in a well-closed environment.

The present invention has an object to stabilize certain benzothia(dia)zepine derivatives in solid formulations containing the same, and provide a solid formulation containing the stabilized derivative mentioned above.

Technical Solution

The object of the present invention can be achieved, in a solid formulation containing (A) a certain benzothia(dia)zepine derivative, by not blending a combination of (b) polyethylene glycol and (C) polyvinyl alcohol, or alternatively, in the case of containing a combination of (b) polyethylene glycol and (C) polyvinyl alcohol in the aforementioned solid formulation, by isolating the aforementioned ingredient (A) from the aforementioned combination of (b) polyethylene glycol and (C) polyvinyl alcohol.

The first aspect of the present invention relates to a solid formulation characterized by comprising:

(A) a compound of formula (I) or (I'):

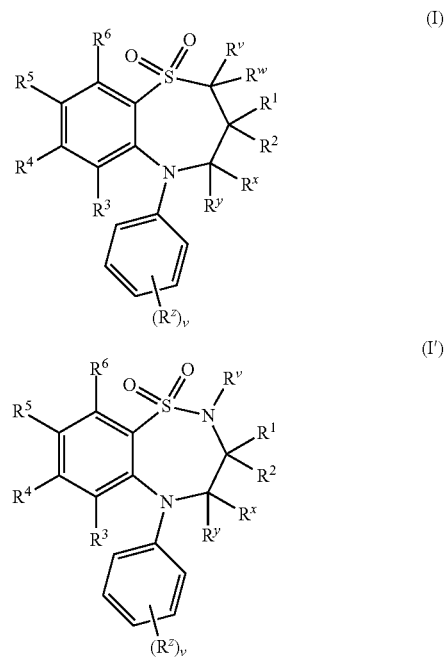

wherein:
R$^v$ and R$^w$ are independently selected from hydrogen or C$_{1-6}$ alkyl;
R$^1$ and R$^2$ are independently selected from C$_{1-6}$ alkyl;
R$^x$ and R$^y$ are independently selected from hydrogen or C$_{1-6}$ alkyl, or one of R$^x$ and R$^y$ is hydrogen or C$_{1-6}$ alkyl and the other is hydroxy or C$_{1-6}$ alkoxy;
R$^z$ is selected from halo, nitro, cyano, hydroxy, amino, carboxy, carbamoyl, mercapto, sulphamoyl, C$_{1-6}$ alkyl, C$_{2-6}$ alkenyl, C$_{2-6}$ alkynyl, C$_{1-6}$ alkoxy, C$_{1-6}$ alkanoyl, C$_{1-6}$ alkanoyloxy, N—(C$_{1-6}$ alkyl)amino, N,N—(C$_{1-6}$ alkyl)$_2$ amino, C$_{1-6}$ alkanoylamino, N—(C$_{1-6}$ alkyl) carbamoyl, N,N—(C$_{1-6}$ alkyl)$_2$ carbamoyl, C$_{1-6}$ alkyl S(O)$_a$ wherein a is 0 to 2, C$_{1-6}$ alkoxycarbonyl, C$_{1-6}$ alkoxycarbonylamino, ureido, N'—(C$_{1-6}$ alkyl) ureido, N—(C$_{1-6}$ alkyl) ureido, N',N'—(C$_{1-6}$ alkyl)$_2$ ureido, N'—(C$_{1-6}$ alkyl)-N—(C$_{1-6}$ alkyl)ureido, N',N'—(C$_{1-6}$ alkyl)$_2$-N—(C$_{1-6}$ alkyl) ureido, N—(C$_{1-6}$ alkyl)sulphamoyl and N,N—(C$_{1-6}$ alkyl)$_2$ sulphamoyl;
v is 0 to 5;

one of $R^4$ and $R^5$ is a group of formula (IA):

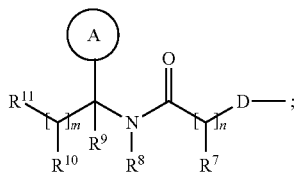

(IA)

$R^3$ and $R^6$, and the other of $R^4$ and $R^5$ are independently selected from hydrogen, halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl)carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl) sulphamoyl and N,N—($C_{1-4}$ alkyl)$_2$ sulphamoyl; wherein $R^3$ and $R^6$ and the other of $R^4$ and $R^5$ may be optionally substituted on carbon by one or more $R^{16}$;

D is —O—, —N($R^a$)—, —S(O)$_b$— or —CH($R^a$)—; wherein $R^a$ is hydrogen or $C_{1-6}$ alkyl and b is 0 to 2;

Ring A is aryl or heteroaryl; wherein Ring A is optionally substituted by one or more substituents selected from $R^{17}$;

$R^7$ is hydrogen, $C_{1-4}$ alkyl, carbocyclyl or heterocyclyl; wherein $R^7$ is optionally substituted by one or more substituents selected from $R^{18}$;

$R^8$ is hydrogen or $C_{1-4}$ alkyl;

$R^9$ is hydrogen or $C_{1-4}$ alkyl;

$R^{10}$ is hydrogen, $C_{1-4}$ alkyl, carbocyclyl or heterocyclyl; wherein $R^{10}$ is optionally substituted by one or more substituents selected from $R^{19}$;

$R^{11}$ is carboxy, sulpho, sulphino, phosphono, tetrazolyl, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$ alkyl; or $R^{11}$ is a group of formula (IB):

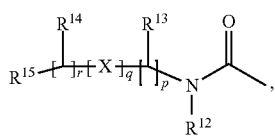

(IB)

wherein:

X is —N(R$^q$)—, —N(R$^q$)C(O)—, —O—, or —S(O)$_a$—; wherein a is 0 to 2 and R$^q$ is hydrogen or $C_{1-4}$ alkyl;

$R^{12}$ is hydrogen or $C_{1-4}$ alkyl;

$R^{13}$ and $R^{14}$ are independently selected from hydrogen, $C_{1-4}$ alkyl, carbocyclyl, heterocyclyl or $R^{23}$; wherein the aforementioned $C_{1-4}$ alkyl, carbocyclyl or heterocyclyl may be independently optionally substituted by one or more substituents selected from $R^{20}$;

$R^{15}$ is carboxy, sulpho, sulphino, phosphono, tetrazolyl, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-6}$ alkyl; or $R^{15}$ is a group of formula (IC):

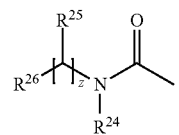

(IC)

wherein:

$R^{24}$ is selected from hydrogen or $C_{1-4}$ alkyl;

$R^{25}$ is selected from hydrogen, $C_{1-4}$ alkyl, carbocyclyl, heterocyclyl or $R^{27}$; wherein said $C_{1-4}$ alkyl, carbocyclyl or heterocyclyl may be independently optionally substituted by one or more substituents selected from $R^{28}$;

$R^{26}$ is selected from carboxy, sulpho, sulphino, phosphono, tetrazolyl, —P(O)(OR$^g$)(OR$^h$), —P(O)(OH)(OR$^9$), —P(O)(OH)(R$^g$) or —P(O)(OR$^g$)(R$^h$) wherein R$^g$ and R$^h$ are independently selected from $C_{1-6}$ alkyl;

p is 1-3; wherein the meanings of $R^{13}$ may be the same or different;

q is 0-1;

r is 0-3; wherein the meanings of $R^{14}$ may be the same or different;

m is 0-2; wherein the meanings of $R^{10}$ may be the same or different;

n is 1-3; wherein the meanings of $R^7$ may be the same or different;

z is 0-3; wherein the meanings of $R^{25}$ may be the same or different;

$R^{16}$, $R^{17}$ and $R^{18}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl)carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl) sulphamoyl and N,N—($C_{1-4}$ alkyl)$_2$ sulphamoyl; wherein $R^{16}$, $R^{17}$ and $R^{18}$ may be independently optionally substituted on carbon by one or more $R^{21}$;

$R^{19}$, $R^{20}$, $R^{23}$, $R^{27}$ and $R^{28}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl) carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl) sulphamoyl, N,N—($C_{1-4}$ alkyl)$_2$ sulphamoyl, carbocyclyl, heterocyclyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$ alkyl; wherein $R^{19}$, $R^{20}$, $R^{23}$, $R^{27}$ and $R^{28}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl, or a pharmaceutically acceptable salt, solvate, or solvate of such a salt, wherein the aforementioned solid formulation is free from a combination of (b) polyethylene glycol and (C) polyvinyl alcohol, or alternatively, in the case of containing a combination of (b) polyethylene glycol and (C) polyvinyl alcohol in the aforementioned solid formulation, the aforementioned ingredient (A) is isolated from the aforementioned combination of (b) polyethylene glycol and (C) polyvinyl alcohol.

The aforementioned solid formulation preferably contains:

at least one core, and at least one coating layer or capsule layer enclosing at least a part of said core, and the aforementioned coating layer or capsule layer is free from a combination of (b) polyethylene glycol and (C) polyvinyl alcohol, or alternatively in the case of the aforementioned coating layer or capsule layer containing a combination of (b) polyethylene glycol and (C) polyvinyl alcohol, at least one isolation layer is provided between the aforementioned core and the aforementioned coating layer or capsule layer.

The aforementioned core preferably contains the aforementioned ingredient (A).

The coating layer or capsule layer can be present in a ratio ranging from 1 to 20% by weight based on the total weight of the solid formulation. In the present specification, the term "weight" has the same meaning as that of "mass". Therefore, "by weight" and "part (s) by weight" have the same meanings as those of "% by mass" and "part(s) by mass", respectively.

The aforementioned coating layer or capsule layer can contain the aforementioned ingredient (b) in an amount ranging from 0.1 to 50% by weight based on the total weight of the coating layer or capsule layer.

The aforementioned coating layer or capsule layer may contain the aforementioned ingredient (C) in an amount ranging from 50 to 90% by weight based on the total weight of the coating layer or capsule layer.

The coating layer or capsule layer preferably further contains at least one selected from the group consisting of a water-soluble polymer other than polyethylene glycol and polyvinyl alcohol, a colorant, a lubricant, and wax.

The water-soluble polymer is preferably hydroxypropyl methylcellulose.

The colorant is preferably selected from the group consisting of titanium oxide, iron oxide, zinc oxide, tar pigment, and lake pigment.

The lubricant is preferably talc.

The wax is preferably carnauba wax.

The core preferably contains at least one additive selected from the group consisting of a filler, a disintegrant, a binder, a lubricant, and a fluidizer.

The solid formulation according to the present invention is preferably a film-coated tablet or a capsule.

The aforementioned ingredient (A) is preferably selected from the group consisting of:

1,1-dioxo-3,3-dibutyl-5-phenyl-7-methylthio-8-(N—{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxy-2-(R)-hydroxypropyl)carbamoyl]-4-hydroxy benzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine; and 1,1-dioxo-3,3-dibutyl-5-phenyl-7-methylthio-8-(N—{(R)-1'-phenyl-1'-[N'-(carboxymethyl)carbamoyl] methyl}carbamoylmethoxy)-2,3,4,5-tetrahydro-1,5-benzothiazepine.

The aforementioned ingredient (A) is more preferably 1,1-dioxo-3,3-dibutyl-5-phenyl-7-methylthio-8-(N—{(R)-1'-phenyl-1'-[N'-(carboxymethyl)carbamoyl] methyl}carbamoylmethoxy)-2,3,4,5-tetrahydro-1,5-benzothiazepine, that is, Elobixibat.

The amount of the aforementioned ingredient (A) may range from 0.01 to 50% by weight based on the total weight of the solid formulation.

The amount of the aforementioned ingredient (A) may range from 1 to 20 mg.

The aforementioned polyethylene glycol preferably has an average molecular weight ranging from 200 to 20,000.

The solid formulation according to the present invention is preferably in the form of a tablet having a diameter ranging from 5 to 11 mm.

The solid formulation according to the present invention is preferably intended for treating or preventing constipation in a warm-blooded animal including a human being. The aforementioned constipation may be functional constipation or constipation-predominant irritable bowel syndrome.

The second aspect of the present invention relates to a method for preventing or reducing coloration of a solid formulation containing (A) a compound of formula (I) or (I'), or a pharmaceutically acceptable salt, solvate, or solvate of such a salt, characterized in that a combination of (b) polyethylene glycol and (C) polyvinyl alcohol is not added to the aforementioned solid formulation, or alternatively, in the case of adding a combination of (b) polyethylene glycol and (C) polyvinyl alcohol to the aforementioned solid formulation, the aforementioned ingredient (A) is isolated from the aforementioned combination of (b) polyethylene glycol and (C) polyvinyl alcohol.

Effects of the Invention

In accordance with the present invention, a certain benzothia(dia)zepine derivative in a solid formulation containing the same can be stabilized, and a solid formulation containing the stabilized derivative can be provided.

The benzothia(dia)zepine derivatives in the solid formulations according to the present invention are stable over time even under an atmosphere at high temperature and/or in high moisture. Therefore, even if the solid formulations according to the present invention are allowed to stand under an atmosphere at high temperature and/or in high moisture, occurrence of coloration (in particular, red coloration phenomenon) of the solid formulations derived due to destabilization of the benzothia(dia)zepine derivatives mentioned above can be prevented or reduced. In particular, the solid formulations of the present invention are stable under well-closed environment.

Therefore, the solid formulations of the present invention can be stored for a long period of time, and the pharmaceutical effects of the benzothia (dia)zepine derivatives contained in the solid formulations can be maintained. In particular, the solid formulations of the present invention can be stable even under an atmosphere at high temperature and/or in high moisture in the summer season.

MODE FOR CARRYING OUT THE INVENTION

As a result of diligent studies of the cause of destabilization of the aforementioned benzothia(dia)zepine derivatives (in particular, red coloration phenomenon) in solid formulations containing the derivatives mentioned above, the inventors of the present application determined the cause. That is, the aforementioned benzothia(dia)zepine derivatives contact a combination of polyethylene glycol and polyvinyl alcohol in the solid formulations, thus causing destabilization of the derivatives.

In the present invention, in a solid formulation containing the aforementioned benzothia(dia)zepine derivative, a combination of polyethylene glycol and polyvinyl alcohol is not added to the solid formulation, or alternatively, in the case of adding a combination of polyethylene glycol and polyvinyl alcohol to the solid formulation, the benzothia(dia)zepine derivative is isolated from the combination of polyethylene glycol and polyvinyl alcohol, thus preventing or reducing destabilization of the benzothia (dia)zepine derivative. Thereby, coloration of the solid formulation derived due to destabilization of the aforementioned benzothia(dia)zepine derivative can be prevented or reduced.

Hereinafter, the embodiments for carrying out the present invention are described in detail.

A first aspect of the present invention relates to a solid formulation containing a certain benzothia(dia)zepine derivative, wherein the solid formulation is free from a combination of polyethylene glycol and polyvinyl alcohol, or alternatively, in the case of containing a combination of polyethylene glycol and polyvinyl alcohol in the solid formulation, the aforementioned benzothia(dia)zepine derivative is isolated from the combination of polyethylene glycol and polyvinyl alcohol.

The benzothia(dia)zepine derivatives usable in the present invention are preferably (A) compounds represented by the following formula (I) or (I'):

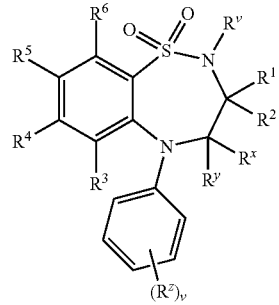

(I)

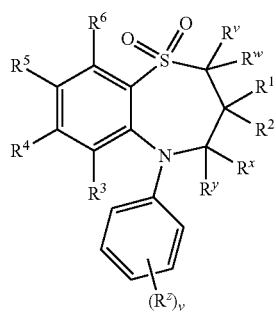

(I')

wherein:
$R^v$ and $R^w$ are independently selected from hydrogen or $C_{1-6}$ alkyl;
$R^1$ and $R^2$ are independently selected from $C_{1-6}$ alkyl;
$R^x$ and $R^y$ are independently selected from hydrogen or $C_{1-6}$ alkyl, or one of $R^x$ and $R^y$ is hydrogen or $C_{1-6}$ alkyl and the other is hydroxy or $C_{1-6}$ alkoxy;
$R^z$ is selected from halo, nitro, cyano, hydroxy, amino, carboxy, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$ amino, $C_{1-6}$ alkanoylamino, N—($C_{1-6}$ alkyl) carbamoyl, N,N—($C_{1-6}$ alkyl)$_2$ carbamoyl, $C_{1-6}$ alkyl S(O)$_a$ wherein a is 0 to 2, $C_{1-6}$ alkoxycarbonyl, $C_{1-6}$ alkoxycarbonylamino, ureido, N'—($C_{1-6}$ alkyl)ureido, N—($C_{1-6}$ alkyl)ureido, N',N'—($C_{1-6}$ alkyl)$_2$ ureido, N'—($C_{1-6}$ alkyl)-N—($C_{1-6}$ alkyl)ureido, N',N'—($C_{1-6}$ alkyl)$_2$-N—($C_{1-6}$ alkyl)ureido, N—($C_{1-6}$ alkyl) sulphamoyl and N,N—($C_{1-6}$ alkyl)$_2$ sulphamoyl;
v is 0 to 5;
one of $R^4$ and $R^5$ is a group of formula (IA):

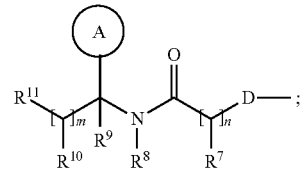

(IA)

$R^3$ and $R^6$, and the other of $R^4$ and $R^5$ are independently selected from hydrogen, halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl)carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl)sulphamoyl and N,N—($C_{1-4}$ alkyl)$_2$ sulphamoyl; wherein $R^3$ and $R^6$ and the other of $R^4$ and $R^5$ may be optionally substituted on carbon by one or more $R^{16}$;
D is —O—, —N($R^a$)—, —S(O)$_b$— or —CH($R^a$)—; wherein $R^a$ is hydrogen or $C_{1-6}$ alkyl and b is 0 to 2;
Ring A is aryl or heteroaryl; wherein Ring A is optionally substituted by one or more substituents selected from $R^{17}$;
$R^7$ is hydrogen, $C_{1-4}$ alkyl, carbocyclyl or heterocyclyl; wherein $R^7$ is optionally substituted by one or more substituents selected from $R^{18}$;

$R^8$ is hydrogen or $C_{1-4}$ alkyl;

$R^9$ is hydrogen or $C_{1-4}$ alkyl;

$R^{10}$ is hydrogen, $C_{1-4}$ alkyl, carbocyclyl or heterocyclyl; wherein $R^{10}$ is optionally substituted by one or more substituents selected from $R^{19}$;

$R^{11}$ is carboxy, sulpho, sulphino, phosphono, tetrazolyl, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$ alkyl; or $R^{11}$ is a group of formula (IB):

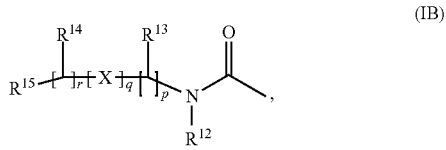

wherein:

X is —N(R$^q$)—, —N(R$^q$)C(O)—, —O—, or —S(O)$_a$—; wherein a is 0 to 2 and R$^q$ is hydrogen or $C_{1-4}$ alkyl;

$R^{12}$ is hydrogen or $C_{1-4}$ alkyl;

$R^{13}$ and $R^{14}$ are independently selected from hydrogen, $C_{1-4}$ alkyl, carbocyclyl, heterocyclyl or $R^{23}$; wherein said $C_{1-4}$ alkyl, carbocyclyl or heterocyclyl may be independently optionally substituted by one or more substituents selected from $R^{20}$;

$R^{15}$ is carboxy, sulpho, sulphino, phosphono, tetrazolyl, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-6}$ alkyl; or $R^{15}$ is a group of formula (IC):

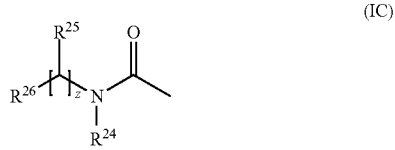

wherein:

$R^{24}$ is selected from hydrogen or $C_{1-4}$ alkyl;

$R^{25}$ is selected from hydrogen, $C_{1-4}$ alkyl, carbocyclyl, heterocyclyl or $R^{27}$; wherein said $C_{1-4}$ alkyl, carbocyclyl or heterocyclyl may be independently optionally substituted by one or more substituents selected from $R^{28}$;

$R^{26}$ is selected from carboxy, sulpho, sulphino, phosphono, tetrazolyl, —P(O)(OR$^g$)(OR$^h$), —P(O)(OH)(OR$^g$), —P(O)(OH)(R$^g$) or —P(O)(OR$^g$)(R$^h$) wherein R$^g$ and R$^h$ are independently selected from $C_{1-6}$ alkyl;

p is 1-3; wherein the meanings of $R^{13}$ may be the same or different;

q is 0-1;

r is 0-3; wherein the meanings of $R^{14}$ may be the same or different;

m is 0-2; wherein the meanings of $R^{10}$ may be the same or different;

n is 1-3; wherein the meanings of $R^7$ may be the same or different;

z is 0-3; wherein the meanings of $R^{25}$ may be the same or different;

$R^{16}$, $R^{17}$ and $R^{18}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl) amino, N,N—($C_{1-4}$ alkyl)$_2$ amino, $C_{1-4}$ alkanoylamino, N—($C_{1-4}$ alkyl)carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl) sulphamoyl and N,N—($C_{1-4}$ alkyl)$_2$ sulphamoyl; wherein $R^{16}$, $R^{17}$ and $R^{18}$ may be independently optionally substituted on carbon by one or more $R^{21}$;

$R^{19}$, $R^{20}$, $R^{23}$, $R^{27}$ and $R^{28}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl)carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl)sulphamoyl, N,N—($C_{1-4}$ alkyl)$_2$ sulphamoyl, carbocyclyl, heterocyclyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$ alkyl; wherein $R^{19}$, $R^{20}$, $R^{23}$, $R^{27}$ and $R^{28}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl, or a pharmaceutically acceptable salt, solvate, or solvate of such a salt; or alternatively a prodrug of the same (hereinafter, simply referred to as "ingredient (A)" in some cases).

The compound of the aforementioned formula (I) is preferably a compound represented by the following formula (I-1):

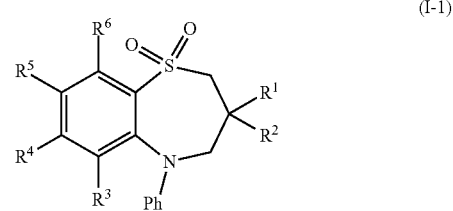

wherein $R^1$ and $R^2$ are independently selected from $C_{1-6}$ alkyl; one of $R^4$ and $R^5$ is a group of the following formula (I-1A'):

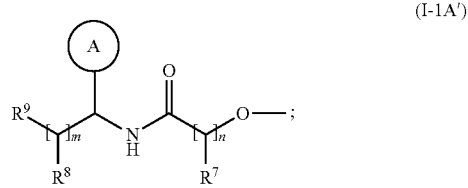

R³ and R⁶, and the other of R⁴ and R⁵ are independently selected from hydrogen, halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl)carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl) sulphamoyl and N,N—($C_{1-4}$ alkyl)$_2$ sulphamoyl; wherein R³ and R⁶ and the other of R⁴ and R⁵ may be optionally substituted on carbon by one or more $R^{12}$;

Ring A is aryl or heteroaryl; wherein Ring A is optionally substituted by one or more substituents selected from $R^{13}$;

R⁷ is hydrogen, $C_{1-4}$ alkyl, carbocyclyl or heterocyclyl; wherein R⁷ is optionally substituted by one or more substituents selected from $R^{14}$;

R⁸ is hydrogen, $C_{1-4}$ alkyl, carbocyclyl or heterocyclyl; wherein R⁸ is optionally substituted by one or more substituents selected from $R^{15}$;

R⁹ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$ alkyl; or R⁹ is a group of formula (I-1B'):

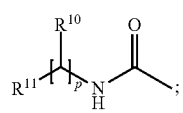

(I-1B')

wherein:
R¹⁰ is selected from hydrogen, $C_{1-4}$ alkyl, carbocyclyl or heterocyclyl; wherein R¹⁰ may be independently optionally substituted by one or more substituents selected from $R^{16}$;

R¹¹ is selected from carboxy, sulpho, sulphino, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-6}$ alkyl;

p is 1-3; wherein the meanings of R¹⁰ may be the same or different;

m is 0-2; wherein the meanings of R⁸ may be the same or different;

n is 1-3; wherein the meanings of R⁷ may be the same or different;

$R^{12}$, $R^{13}$ and $R^{14}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl) amino, N,N—($C_{1-4}$ alkyl)$_2$ amino, $C_{1-4}$ alkanoylamino, N—($C_{1-4}$ alkyl)carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl)sulphamoyl and N,N—($C_{1-4}$ alkyl)$_2$ sulphamoyl;

wherein $R^{12}$, $R^{13}$ and $R^{14}$ may be independently optionally substituted on carbon by one or more $R^{17}$;

$R^{15}$ and $R^{16}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl)carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl)sulphamoyl, N,N—($C_{1-4}$ alkyl)$_2$ sulphamoyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$ alkyl; wherein $R^{15}$ and $R^{16}$ may be independently optionally substituted on carbon by one or more $R^{18}$;

$R^{17}$ and $R^{18}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl.

The compound of the aforementioned formula (I) is more preferably a compound represented by the following formula (I-2):

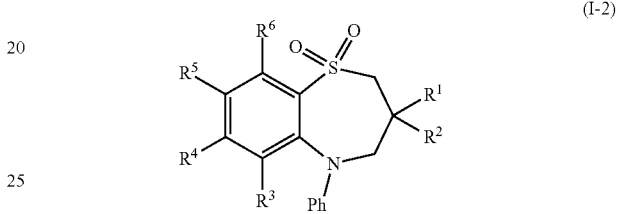

(I-2)

wherein
R¹ and R² are independently selected from $C_{1-6}$ alkyl; one of R⁴ and R⁵ is a group of the following formula (I-2A"):

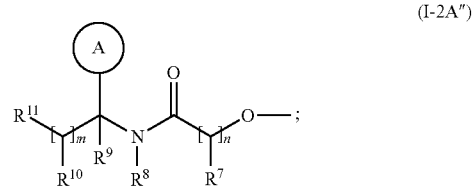

(I-2A")

R³ and R⁶, and the other of R⁴ and R⁵ are independently selected from hydrogen, halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl)carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl) sulphamoyl and N,N—($C_{1-4}$ alkyl)$_2$ sulphamoyl; wherein R³ and R⁶ and the other of R⁴ and R⁵ may be optionally substituted on carbon by one or more $R^{16}$;

Ring A is aryl or heteroaryl; wherein Ring A is optionally substituted by one or more substituents selected from $R^{17}$;

R⁷ is hydrogen, $C_{1-4}$ alkyl, carbocyclyl or heterocyclyl; wherein R⁷ is optionally substituted by one or more substituents selected from $R^{18}$;

R⁸ is hydrogen or $C_{1-4}$ alkyl;

R⁹ is hydrogen or $C_{1-4}$ alkyl;

R¹⁰ is hydrogen, $C_{1-4}$ alkyl, carbocyclyl or heterocyclyl; wherein R¹⁰ is optionally substituted by one or more substituents selected from $R^{19}$;

R¹¹ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$ alkyl; or R¹¹ is a group of formula (I-2B"):

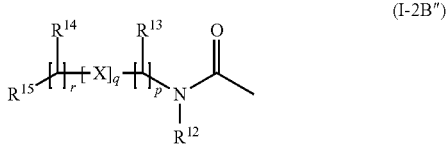

(I-2B″)

wherein

X is —N($R^q$)—, —N($R^q$) C(O)—, —O—, or —S(O)$_a$— wherein a is 0 to 2 and $R^q$ is hydrogen or $C_{1-4}$ alkyl;

$R^{12}$ is hydrogen or $C_{1-4}$ alkyl;

$R^{13}$ and $R^{14}$ are independently selected from hydrogen, $C_{1-4}$ alkyl, carbocyclyl or heterocyclyl; wherein $R^{13}$ and $R^{14}$ are optionally substituted by one or more substituents selected from $R^{20}$;

$R^{15}$ is carboxy, sulpho, sulphino, phosphono, —P(O)(OR$^e$)(OR$^e$), —P(O)(OH)(OR$^e$), —P(O)(OH)(R$^e$) and —P(O)(OR$^e$)(R$^f$) wherein R$^e$ and R$^f$ are independently selected from $C_{1-6}$ alkyl;

p is 1-3; wherein the meanings of $R^{13}$ may be the same or different; q is 0-1;

r is 0-3; wherein the meanings of $R^{14}$ may be the same or different;

m is 0-2; wherein the meanings of $R^{10}$ may be the same or different;

n is 1-3; wherein the meanings of $R^7$ may be the same or different;

$R^{16}$, $R^{17}$ and $R^{18}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl) amino, N,N—($C_{1-4}$ alkyl)$_2$ amino, $C_{1-4}$ alkanoylamino, N—($C_{1-4}$ alkyl)carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl)sulphamoyl and N,N—($C_{1-4}$ alkyl)$_2$ sulphamoyl;

wherein $R^{16}$, $R^{17}$ and $R^{18}$ may be independently optionally substituted on carbon by one or more $R^{21}$;

$R^{19}$ and $R^{20}$ are independently selected from halo, nitro, cyano, hydroxy, amino, carboxy, carbamoyl, mercapto, sulphamoyl, $C_{1-4}$ alkyl, $C_{2-4}$ alkenyl, $C_{2-4}$ alkynyl, $C_{1-4}$ alkoxy, $C_{1-4}$ alkanoyl, $C_{1-4}$ alkanoyloxy, N—($C_{1-4}$ alkyl)amino, N,N—($C_{1-4}$ alkyl)$_2$ amino, $C_{1-4}$ alkanoylamino, N—($C_{1-4}$ alkyl)carbamoyl, N,N—($C_{1-4}$ alkyl)$_2$ carbamoyl, $C_{1-4}$ alkyl S(O)$_a$ wherein a is 0 to 2, $C_{1-4}$ alkoxycarbonyl, N—($C_{1-4}$ alkyl)sulphamoyl, N,N—($C_{1-4}$ alkyl)$_2$ sulphamoyl, carbocyclyl, heterocyclyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$ alkyl; wherein $R^{19}$ and $R^{20}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl.

Hereinafter, in the case of indicating a compound of formula (I), it should be understood that the aspect thereof also relates to the compounds of formula (I-1) and the compounds of formula (I-2).

In addition, a person having ordinary skill in the art will recognize that the numbering system differs between the compounds of formula (I) and the compounds of formula (I-1). The numbering system used hereinafter in the present specification refers to the compounds of formula (I). However, it should be understood that such a numbering system is also applied to the meanings corresponding to those of formula (I-1).

In the present specification, the term "alkyl" includes both straight and branched chain alkyl groups, but the references to individual alkyl groups such as "propyl" are specific for the straight chain version only. For example, "$C_{1-6}$ alkyl" includes $C_{1-4}$ alkyl, $C_{1-3}$ alkyl, propyl, isopropyl and t-butyl. However, references to individual alkyl groups such as 'propyl' are specific for the straight-chain version only and references to individual branched chain alkyl groups such as 'isopropyl' are specific for the branched chain version only. A similar convention applies to other radicals, for example "phenyl $C_{1-6}$ alkyl" would include phenyl $C_{1-4}$ alkyl, benzyl, 1-phenylethyl and 2-phenylethyl. The term "halo" refers to fluoro, chloro, bromo and iodo.

In the case where optional substituents are chosen from "one or more" groups, it should be understood that such a definition includes all substituents being chosen from one of the specified groups or chosen from two or more of the specified groups.

"Heteroaryl" is a totally unsaturated, monocyclic or bicyclic ring containing 3-12 atoms of which at least one atom is chosen from nitrogen, sulfur or oxygen, and which may, unless otherwise specified, be carbon- and nitrogen-linked. A preferable "heteroaryl" refers to a totally unsaturated, monocyclic ring containing 5 or 6 atoms or a totally unsaturated, bicyclic ring containing 9 or 10 atoms of which at least one atom is chosen from nitrogen, sulfur and oxygen, and which may, unless otherwise specified, be carbon- or nitrogen-linked. In another aspect of the present invention, "heteroaryl" refers to a totally unsaturated, monocyclic ring containing 5 or 6 atoms or a totally unsaturated, bicyclic ring containing 8, 9 or 10 atoms of which at least one atom is chosen from nitrogen, sulfur and oxygen, and which may, unless otherwise specified, be carbon- or nitrogen-linked. Examples and suitable meanings of the term "heteroaryl" are thienyl, isoxazolyl, imidazolyl, pyrrolyl, thiadiazolyl, isothiazolyl, triazolyl, pyranyl, indolyl, pyrimidyl, pyrazinyl, pyridazinyl, pyridyl and quinolyl. The term "heteroaryl" preferably refers to thienyl or indolyl.

"Aryl" is a totally unsaturated, mono or bicyclic carbon ring that contains 3-12 atoms. Preferable "aryl" is a monocyclic ring containing 5 or 6 atoms or a bicyclic ring containing 9 or 10 atoms. Suitable meanings for "aryl" include phenyl or naphthyl. "Aryl" is more preferably phenyl.

"Heterocyclyl" is a saturated, partially saturated or unsaturated, mono or bicyclic ring containing 3-12 atoms of which at least one atom is chosen from nitrogen, sulfur and oxygen, and which may, unless otherwise specified, be carbon- or nitrogen-linked, wherein a —CH$_2$— group can optionally be replaced by a —C(O)—, or a ring sulfur atom may be optionally oxidized to form S-oxide. Preferably "heterocyclyl" is a saturated, partially saturated or unsaturated, mono or bicyclic ring containing 5 or 6 atoms of which at least one atom is chosen from nitrogen, sulfur and oxygen, and which may, unless otherwise specified, be carbon- or nitrogen-linked, wherein a —CH$_2$— group can optionally be replaced by a —C(O)— or a ring sulfur atom may be optionally oxidized to form S-oxide(s). Examples and suitable meanings of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo[2.2.1] heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrinidyl, thiazolyl, pyrazinyl, pyridazinyl, pyridyl, 4-pyridonyl, quinolyl and 1-isoquinolonyl.

"Carbocyclyl" is a saturated, partially saturated or unsaturated, mono or bicyclic carbon ring that contains 3-12 atoms; wherein a —CH$_2$— group can optionally be replaced by a —C(O)—. Preferable "carbocyclyl" is a monocyclic ring containing 5 or 6 atoms or a bicyclic ring containing 9 or 10 atoms. Suitable meanings for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. In particular, "carbocyclyl" is cyclopropyl, cyclobutyl, 1-oxocyclopentyl, cyclopentyl, cyclopentenyl, cyclohexyl, cyclohexenyl, phenyl or 1-oxoindanyl.

An example of "$C_{1-6}$ alkanoyloxy" and "$C_{1-4}$ alkanoyloxy" is acetoxy. Examples of "$C_{1-6}$ alkoxycarbonyl" and "$C_{1-4}$ alkoxycarbonyl" include methoxycarbonyl, ethoxycarbonyl, and n- and t-butoxycarbonyl. Examples of "$C_{1-6}$ alkoxy" and "$C_{1-4}$ alkoxy" include methoxy, ethoxy and propoxy. Examples of "$C_{1-6}$ alkanoylamino" and "$C_{1-4}$ alkanoylamino" include formamido, acetamido and propionylamino. Examples of "$C_{1-6}$ alkyl S(O)$_a$ wherein a is 0 to 2" and "$C_{1-4}$ alkyl S(O)$_a$ wherein a is 0 to 2" include methylthio, ethylthio, methylsulphinyl, ethylsulphinyl, mesyl and ethylsulphonyl. Examples of "$C_{1-6}$ alkanoyl" and "$C_{1-4}$ alkanoyl" include $C_{1-3}$ alkanoyl, propionyl and acetyl. Examples of "N—($C_{1-6}$ alkyl)amino" and "N—($C_{1-4}$ alkyl) amino" include methylamino and ethylamino. Examples of "N,N—($C_{1-6}$ alkyl)$_2$ amino" and "N,N—($C_{1-4}$ alkyl)$_2$ amino" include di-N-methylamino, di-(N-ethyl)amino and N-ethyl-N-methylamino. Examples of "$C_{2-6}$ alkenyl" and "$C_{2-4}$ alkenyl" are vinyl, allyl and 1-propenyl. Examples of "$C_{2-6}$ alkynyl" and "$C_{2-4}$ alkynyl" are ethynyl, 1-propynyl and 2-propynyl. Examples of "N—($C_{1-6}$ alkyl) sulphamoyl" and "N—($C_{1-4}$ alkyl)sulphamoyl" are N—($C_{1-3}$ alkyl)sulphamoyl, N-(methyl)sulphamoyl and N-(ethyl)sulphamoyl. Examples of "N—($C_{1-6}$ alkyl)$_2$ sulphamoyl" and "N—($C_{1-4}$ alkyl)$_2$ sulphamoyl" are N,N-(dimethyl)sulphamoyl and N-(methyl)-N-(ethyl)sulphamoyl. Examples of "N—($C_{1-6}$ alkyl)carbamoyl" and "N—($C_{1-4}$ alkyl)carbamoyl" are methylaminocarbonyl and ethylaminocarbonyl. Examples of "N,N—($C_{1-6}$ alkyl)$_2$ carbamoyl" and "N,N—($C_{1-4}$ alkyl)$_2$ carbamoyl" are dimethylaminocarbonyl and methylethylaminocarbonyl. Examples of "$C_{1-6}$ alkoxycarbonylamino" are ethoxycarbonylamino and t-butoxycarbonylamino. Examples of "N'—($C_{1-6}$ alkyl)ureido" are N'-methylureido and N'-ethylureido. Examples of "N—($C_{1-6}$ alkyl)ureido" are N-methylureido and N-ethylureido. Examples of "N',N'—($C_{1-6}$ alkyl)$_2$ ureido" are N',N'-dimethylureido and N'-methyl-N'-ethylureido. Examples of "N'—($C_{1-6}$ alkyl)-N—($C_{1-6}$ alkyl)ureido" are N'-methyl-N-methylureido and N'-propyl-N-methylureido. Examples of "N',N'—($C_{1-6}$ alkyl)$_2$-N($C_{1-6}$ alkyl)ureido" are N',N'-dimethyl-N-methylureido and N'-methyl-N'-ethyl-N-propylureido.

A suitable pharmaceutically acceptable salt of the compound of the present invention mentioned above is, for example, an acid-addition salt of a compound of the present invention which is sufficiently basic, such as an acid-addition salt with, for example, an inorganic or organic acid, such as hydrochloric acid, hydrobromic acid, sulphuric acid, phosphoric acid, trifluoroacetic acid, citric acid or maleic acid. In addition, a suitable pharmaceutically acceptable salt of a compound of the present invention which is sufficiently acidic is an alkali metal salt such as a sodium or potassium salt, an alkaline earth metal salt such as a calcium or magnesium salt, an ammonium salt or a salt with an organic base which affords a physiologically-acceptable cation, for example, a salt with methylamine, dimethylamine, trimethylamine, piperidine, morpholine or tris-(2-hydroxyethyl) amine.

The compounds of formula (I) may be administered in the form of a pro-drug which is decomposed in the human or animal body to give a compound of formula (I). Examples of pro-drugs include in vivo hydrolysable esters and in vivo hydrolysable amides of a compound of formula (I).

An in vivo hydrolysable ester of a compound of formula (I) containing a carboxy or hydroxy group is, for example, a pharmaceutically acceptable ester which is hydrolyzed in the human or animal body to produce the parent acid or alcohol. Suitable pharmaceutically acceptable esters for carboxy include $C_{1-6}$ alkoxymethyl esters such as methoxymethyl, $C_{1-6}$ alkanoyloxymethyl esters such as pivaloyloxymethyl, phthalidyl esters, $C_{3-8}$ cycloalkoxycarbonyloxy $C_{1-6}$ alkyl esters such as 1-cyclohexylcarbonyloxyethyl; 1,3-dioxolen-2-onylmethyl esters such as 5-methyl-1,3-dioxolen-2-onylmethyl; and $C_{1-6}$ alkoxycarbonyloxyethyl esters such as 1-methoxycarbonyloxyethyl, and may be formed at any carboxy group in the compounds of the present invention.

An in vivo hydrolysable ester of a compound of formula (I) containing a hydroxy group includes inorganic esters such as phosphate esters and alpha-acyloxyalkyl ethers and related compounds which as a result of the in vivo hydrolysis of the ester decomposed to give the parent hydroxy group. Examples of alpha-acyloxyalkyl ethers include acetoxymethoxy and 2,2-dimethylpropionyloxy-methoxy. A selection of in vivo hydrolysable ester-forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable meaning for an in vivo hydrolysable amide of a compound of formula (I) containing a carboxy group is, for example, an N—$C_{1-6}$ alkyl or N,N-di-$C_{1-6}$ alkyl amide such as N-methyl, N-ethyl, N-propyl, N,N-dimethyl, N-ethyl-N-methyl or N,N-diethyl amide.

The compounds mentioned above have IBAT inhibitory activities. Some compounds of formula (I) may have chiral centers and/or geometric isomeric centers (E- and Z-isomers), and it should be understood that the present invention encompasses all such optical, diastereoisomers and geometric isomers that possess IBAT inhibitory activities.

The aforementioned ingredient (A) in the present invention relates to any and all tautomeric forms of the compounds of formula (I) that possess IBAT inhibitory activities.

It should also be understood that certain compounds of formula (I) can exist in the solvated as well as unsolvated forms such as a hydrated form. It should be understood that the ingredient (A) mentioned above in the present invention encompasses all such solvated forms which possess IBAT inhibitory activities.

More preferable compounds as a compound of formula (I) are represented by the following formula (I-3):

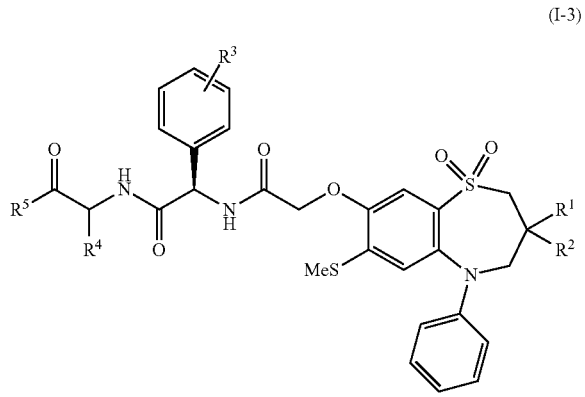

(I-3)

wherein:
$R^1$ and $R^2$ are independently selected from $C_{1-4}$ alkyl;
$R^3$ is hydrogen, hydroxy or halo;
$R^4$ is hydrogen or $C_{1-4}$ alkyl which may be substituted by hydroxy, methoxy and methyl $S(O)_a$ wherein a is 0 to 2;
$R^5$ is hydroxy or $HOC(O)CH(R^6)NH$—;
$R^6$ is selected from hydrogen and $C_{1-3}$ alkyl which may be substituted by hydroxy, methoxy and methyl $S(O)_a$ wherein a is 0 to 2;
with the proviso that in the case where both $R^1$ and $R^2$ are butyl, $R^5$ is hydroxy, and $R^4$ is methylthiomethyl, methylsulfinylmethyl, 2-methylthioethyl, hydroxymethyl, or methoxymethyl, $R^3$ is not hydrogen; and with the proviso that in the case where both $R^1$ and $R^2$ are butyl, $R^5$ is $HOC(O)CH(R^6)NH$—, and $R^6$ is hydroxymethyl, and $R^4$ is hydroxymethyl, $R^3$ is not hydrogen.

As the compound of formula (I), in particular, 1,1-dioxo-3,3-dibutyl-5-phenyl-7-methylthio-8-(N—{(R)-1'-phenyl-1'-[N'-(carboxymethyl)carbamoyl]methyl}carbamoylmethoxy)-2,3,4,5-tetrahydro-1,5-benzothiadiazepine, that is, Elobixibat is preferable.

On the other hand, as the compound of formula (I'), in particular, 1,1-dioxo-3,3-dibutyl-5-phenyl-7-methylthio-8-(N—{(R)-α-[N-(2-sulphoethyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine; 1,1-dioxo-3,3-dibutyl-5-phenyl-7-methylthio-8-(N—{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine; or 1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine is preferable.

A compound of formula (I) or (I'), or a pharmaceutically acceptable salt, solvate, solvate of such a salt or a prodrug thereof can be manufactured in accordance with a method described in, for example, Japanese Patent No. 3665005 (the content of which is incorporated in the specification of the present application by reference).

The aforementioned ingredient (A) possesses IBAT inhibitory activities. These properties may be assessed, for example, using an in vitro test assay for studying the effect on bile acid uptake in IBAT-transfected cells (Smith L., Price-Jones M. J., Hugnes K. T., and Jones N. R. A.; J Biomolecular Screening, 3, 227-230) or in vivo by studying the effect on radiolabelled bile acid absorption in mice/rats (Lewis M. C., Brieaddy L. E. and Root C., J., J Lip Res 1995, 36, 1098-1105).

The aforementioned ingredient can be used in the treatment of dyslipidemic conditions and disorders such as hyperlipidemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as a human being.

In addition, the aforementioned ingredient (A) can be used in the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocyte, monocytes and/or macrophage infiltrate, intimital thickening, medial thinning, infectious and surgical trauma and vascular thrombosis, stroke and transient ischemic attacks in a warm-blooded animal, such as a human being.

There is evidence indicating that an IBAT inhibitor can be potentially useful in the treatment and/or prevention of gallstone or cholelithiasis. The aforementioned ingredient (A) can be used in the treatment and/or prevention of gallstone or cholelithiasis in a warm-blooded animal, such as a human being.

In the present invention, the aforementioned ingredient (A) can also be used in the treatment of gastrointestinal disorders. In particular, the ingredient (A) can be used in the treatment of chronic constipation, functional constipation and irritable bowel syndrome, and in particular, constipation-dominant irritable bowel syndrome (C-IBS).

In the specification of the present application, in the case of using the terms "functional constipation" and "C-IBS", it should be understood that they are defined in accordance with "Rome 2 Criteria" (Gut 45 (Suppl 2): 43, 1999, II43-II47).

An amount of the aforementioned ingredient (A) contained in the solid formulation of the present invention is not particularly limited, and can range from 0.01 to 50% by weight, preferably ranges from 0.05 to 40% by weight, more preferably ranges from 0.1 to 30% by weight, even more preferably ranges from 0.2 to 20% by weight, even more preferably ranges from 0.5 to 10% by weight, and in particular, preferably ranges from 0.8 to 5% by weight, based on the total weight of the solid formulation.

An amount of the aforementioned ingredient (A) contained in the solid formulation of the present invention is not particularly limited, and can range from 0.1 to 100 mg, preferably ranges from 0.3 to 75 mg, more preferably ranges from 0.5 to 50 mg, even more preferably ranges from 0.8 to 30 mg, and in particular, preferably ranges from 1 to 20 mg.

Polyethylene glycol (b) (hereinafter, simply referred to as "ingredient (b)" in some cases) in the first aspect of the present invention has an average molecular weight preferably ranging from 200 to 20,000, more preferably ranging from 300 to 10,000, and even more preferably ranging from 400 to 6,000. The average molecular weight used herein may be a number average molecular weight.

Polyvinyl alcohol (C) (hereinafter, simply referred to as "ingredient (C)" in some cases) in the first aspect of the present invention is not particularly limited as long as it can be usually used for film-coating a medicinal product, and may be either one of completely hydrolyzed product or partially hydrolyzed product. As a partially hydrolyzed product, for example, a product having a degree of hydrolyzation ranging from 70 to 95% by mol, in particular, ranging from 80 to 90% by mol, or furthermore ranging from 85 to 90% by mol is preferably used. In addition, a degree of polymerization is not particularly limited, but preferably ranges from 100 to 3,000, and more preferably ranges from 300 to 1,000.

In the first aspect of the present invention, a solid formulation containing ingredient (A) is free from a combination of (b) polyethylene glycol and (C) polyvinyl alcohol, or in the case where a solid formulation contains a combination of (b) polyethylene glycol and (C) polyvinyl alcohol, the aforementioned ingredient (A) is isolated from the combination of (b) polyethylene glycol and (C) polyvinyl alcohol.

The term "free from" means that does not substantially exist in a solid formulation of the present invention. Therefore, a trace amount of the aforementioned ingredient (b) and ingredient (C) may coexist within a range in which coloration of the solid formulation of the present invention can be prevented or reduced. More particularly, even if ingredient (A) is able to contact a combination of ingredient (b) and ingredient (C), the aforementioned ingredient (b) may exist in an amount of less than 1% by weight based on the total weight of the solid formulation, or may exist in an amount of less than 0.1% by weight or in an amount of less than 0.01% by weight, based on the total weight of the solid formulation. In addition, even if ingredient (A) is able to contact a combination of ingredient (b) and ingredient (C), the aforementioned ingredient (C) may exist in an amount of less than 10% by weight based on the total weight of the solid formulation, or may exist in an amount of less than 5% by weight based on the total weight of the solid formulation, or may exist in an amount of less than 1% by weight, based on the total weight of the solid formulation.

A particular embodiment of isolation in the case of isolating ingredient (A) from the combination of ingredient (b) and ingredient (C) is not particularly limited, and any options can be used as long as direct contact between ingredient (A) and the combination of ingredient (b) and ingredient (C) is inhibited. For example, at least one isolation layer can be provided between ingredient (A), and one or both of ingredient (b) and ingredient (C).

The material of the isolation layer mentioned above is not particularly limited, as long as the material does not include both ingredient (b) and ingredient (C). For example, the material of the isolation layer may be a water-soluble polymer of a cellulose derivative such as hydroxypropyl methylcellulose (hypromellose) or hydroxypropyl cellulose, a water-soluble vinyl derivative (such as polyvinyl alcohol), or a water-soluble polymer such as polyethylene glycol or starch. In addition, as a material of the isolation layer mentioned above, a lubricant such as calcium stearate, glycerol monostearate, glyceryl palmitostearate, magnesium stearate, sodium stearyl fumarate, sucrose fatty acid ester, zinc stearate, stearic acid, or talc can also be used. In addition, a coating agent such as titanium oxide can also be used. In order to achieve assured isolation, a water-soluble polymer is preferably used, and use of hypromellose is more preferable.

Weight of the isolation layer mentioned above is not particularly limited. An amount of the isolation layer preferably ranges from 0.1 to 20% by weight, more preferably ranges from 0.5 to 15% by weight, and even more preferably ranges from 1 to 10% by weight, based on the total weight of the solid formulation.

Thickness of the isolation layer mentioned above is not particularly limited, and preferably ranges from 0.01 to 5 mm, more preferably ranges from 0.05 to 3 mm, and even more preferably ranges from 0.1 to 1 mm.

In the case of isolating ingredient (A) from a combination of ingredient (b) and ingredient (C), the amount of the aforementioned ingredient (b) and ingredient (C) contained in a solid formulation of the present invention is not limited.

In the case of ingredient (A) being isolated from a combination of ingredient (b) and ingredient (C), the amount of ingredient (b) contained in the solid formulation of the present invention can range, for example, from 0.1 to 20% by weight, and may range from 0.2 to 10% by weight, or may range from 0.3 to 5% by weight, based on the total weight of the solid formulation. In addition, the amount of ingredient (b) contained in the solid formulation of the present invention can range, for example, from 1 to 50% by weight, or may range from 3 to 45% by weight, or may range from 5 to 40% by weight, based on the total weight of the aforementioned ingredient (A).

In the case of ingredient (A) being isolated from a combination of ingredient (b) and ingredient (C), the amount of ingredient (C) contained in the solid formulation of the present invention can range, for example, from 0.1 to 20% by weight, may range from 1.0 to 10% by weight, or may range from 2.0 to 5% by weight, based on the total weight of the solid formulation. In addition, the amount of ingredient (C) contained in the solid formulation of the present invention can range, for example, from 10 to 80% by weight, may range from 20 to 75% by weight, or may range from 30 to 50% by weight, based on the total weight of the aforementioned ingredient (A).

The solid formulation preferably contains
at least one core, and
at least one coating layer or capsule layer enclosing at least a part of the aforementioned core, and
the aforementioned coating layer or capsule layer is free from a combination of (b) polyethylene glycol and (C) polyvinyl alcohol, or alternatively,
in the case of the aforementioned coating layer or capsule layer containing a combination of (b) polyethylene glycol and (C) polyvinyl alcohol, at least one isolation layer is provided between the core and the coating layer or capsule layer.

Only one core may be present in the solid formulation of the present invention, or two or more cores may be present. The core preferably contains ingredient (A). The form of the core is not particularly limited, and the core may be in the form of a mixture of simple powders, granules or the like. On the other hand, in the case of the solid formulation of the present invention being in the form of a film-coated tablet, the core mentioned above can be an uncoated tablet before film-coating. In addition, in the case of the solid formulation of the present invention being in the form of a capsule tablet, the aforementioned core can form a granule to be capsulated.

The aforementioned core preferably contains an inert carrier together with ingredient (A). The inert carrier mentioned above preferably contains at least one additive selected from the group consisting of a filler, a disintegrant, a binder, a lubricant, and a fluidizer.

As the filler, at least one selected from the group consisting of sugars, sugar alcohols, inorganic fillers and crystalline cellulose is preferable. Examples of sugars include, for example, lactose (lactose hydrate, anhydrous lactose), saccharose, sucrose, fructose, fructooligosaccharides, glucose, maltose, reduced maltose, powder sugar, powdered candy, reduced lactose, and the like. Examples of sugar alcohols include, for example, erythritol, sorbitol, maltitol, xylitol, mannitol, and the like. Examples of inorganic fillers include, for example, anhydrous calcium hydrogen phosphate, anhydrous calcium phosphate, precipitated calcium carbonate, calcium silicate, and the like. A combination of two or more types among these may be used. Mannitol, crystalline cellulose, or a mixture thereof is preferable. An amount of the filler in the core mentioned above is not particularly limited, usually ranges from 60 to 99% by weight, preferably ranges from 70 to 95% by weight, and more preferably ranges from 80 to 90% by weight based on the total weight of the core.

As the disintegrant, at least one selected from the group consisting of natural starches, starch derivatives, crospovidone, carboxymethyl cellulose, carboxymethyl cellulose calcium, low-substituted hydroxypropyl cellulose and carmellose is preferable. For example, examples of natural starches include corn starch, potato starch, rice starch, wheat starch and the like. Examples of starch derivatives include hydroxypropyl starch obtained by processing the natural starch, and the like. A combination of two or more types among these may be used. Carmellose is preferable, croscarmellose is more preferable, and croscarmellose sodium is even more preferable. An amount of the disintegrant in the aforementioned core is not particularly limited, but usually ranges from 0.1 to 20% by weight, preferably ranges from 1.0 to 10% by weight, and more preferably ranges from 2.0 to 5% by weight based on the total weight of the core.

Examples of the binder include, for example, hydroxypropyl cellulose, polyvinyl alcohol, povidone (polyvinylpyrrolidone), hypromellose (hydroxypropyl methylcellulose), agar, gelatin and the like. A combination of two or more types among these may be used. Hypromellose is preferable. An amount of the binder in the aforementioned core is not particularly limited, but usually ranges from 0.1 to 20% by weight, preferably ranges from 1.0 to 10% by weight, and more preferably ranges from 2.0 to 5% by weight.

Examples of the lubricant include, for example, calcium stearate, glycerol monostearate, glyceryl palmitostearate, magnesium stearate, sodium stearyl fumarate, sucrose fatty acid ester, zinc stearate, stearic acid, talc, and the like. A combination of two or more types among these may be used. Magnesium stearate is preferable. An amount of the lubricant in the core is not particularly limited, but usually ranges from 0.1 to 20% by weight, preferably ranges from 0.5 to 10% by weight, and more preferably ranges from 1.0 to 5% by weight based on the total weight of the core.

Examples of fluidizer include, for example, light anhydrous silicic acid, hydrated silicon dioxide, and the like. A combination of two or more types among these may be used. Light anhydrous silicic acid is preferable. An amount of the fluidizer in the core is not particularly limited, but usually ranges from 0.01 to 10% by weight, preferably ranges from 0.1 to 5% by weight, and more preferably ranges from 0.5 to 3% by weight based on the total weight of the core.

In order to provide good administration ability in the oral cavity, a sweetener and/or a flavoring agent or a perfuming agent may preferably be added to the aforementioned core. Examples of the sweetener include, for example, dipotassium glycyrrhizinate, saccharin sodium, saccharin, stevia, aspartame, sucralose, thaumatin, acesulfame-K, neotame, and the like. Examples of the flavoring agent or the perfuming agent include, for example, citrus flavors of lemon, orange, grapefruit, and the like, peppermint, spearmint, menthol, pine, cherry, fruit, yogurt, coffee, and the like.

In the core mentioned above, non-toxic and inert additives commonly used in the formulation field can be added within the range which does not affect the effects of the present invention. Examples of the additive used include, for example, a surfactant, an organic acid, a colorant, and the like.

A method for producing the core mentioned above is not particularly limited. For example, in the case of the core mentioned above being in the form of a granule, the core can be manufactured by means of a fluid bed granulator represented by a flow coater (manufactured by Freund Corp.), a GPCG (Glatt Powder Coater Granulator), a WSG (Wirbel Schicht Granulator), a multiplex (GLATT/manufactured by Powrex Corporation), or the like, or by means of a stirring granulator represented by a vertical granulator (manufactured by Powrex Corporation), or the like.

In addition, in the case of the core mentioned above being in the form of an uncoated tablet, a wet granulation tableting method in which the granules manufactured by means of the aforementioned manufacturing method are molded, a direct tableting method in which various raw materials are suitably mixed, and the mixed powder is molded, or a dry granulation tableting method can be used. As the molding method mentioned above, a compression molding method using a rotary tableting machine or the like is preferable from a commercial point of view. The uncoated tablet can also be molded by means of an external lubricating method. In this case, tableting is carried out after mixing the ingredients other than a lubricant, while spraying the lubricant on a die-punch, or alternatively, tableting is carried out after previously mixing a part of the lubricant with the ingredients other than a lubricant, by spraying the remaining lubricant on a die-punch. In addition, the uncoated tablet can also be manufactured by means of a special tablet press such as a tablet press for nucleated tablets, a two-layer tablet press, or a three-layer tablet press.

In the case of the core mentioned above being an uncoated tablet, in order to maintain a good balance between disintegration time and hardness, a suitable tableting pressure is preferably selected during production of the uncoated tablets. The tableting pressure is normally 2 kN (about 200 kgf) or more, preferably 4 kN (about 400 kgf) or more, and more preferably 6 kN (about 600 kgf) or more.

In the solid formulation of the present invention according to the aforementioned embodiment, only one coating layer or capsule layer mentioned above enclosing the core mentioned above may be present, or two or more coating layers or capsule layers may be present. Here, "enclosing" means that the coating layer or capsule layer encloses the core, and does not necessarily contact the core. For example, at least one isolating layer may be present between the core and the coating layer or capsule layer. In this case, the core does not directly contact the coating layer or capsule layer. On the other hand, the core may directly contact the coating layer or capsule layer. In this case, the coating layer or capsule layer contains neither ingredient (b) nor ingredient (C). On the other hand, even if the core directly contacts the coating layer or capsule layer, the coating layer or capsule layer can contain either one of ingredient (b) or ingredient (C).

The weight of the isolation layer mentioned above is not particularly limited, and preferably ranges from 0.1 to 20% by weight, more preferably ranges from 0.5 to 15% by weight, and even more preferably ranges from 1 to 10% by weight based on the total weight of the solid formulation.

The thickness of the isolation layer mentioned above is not particularly limited, and preferably ranges from 0.01 to 5 mm, more preferably ranges from 0.05 to 3 mm, and even more preferably ranges from 0.1 to 1 mm.

The coating layer or capsule layer mentioned above can be present in a ratio ranging from 0.1 to 20% by weight, preferably ranging from 0.5 to 15% by weight and further more ranging from 1 to 10% by weight based on the total weight of the solid formulation.

The coating layer or capsule layer mentioned above may include a small amount of ingredient (A). In this case, an amount of the aforementioned ingredient (A) included therein is preferably 10% by weight or less, more preferably 5% by weight or less, more preferably 1% by weight or less, and even more preferably 0.1% by weight or less, based on the total weight of the aforementioned layer. In particular, preferably, the coating layer or capsule layer mentioned above does not contain ingredient (A).

The coating layer or capsule layer mentioned above can contain ingredient (b) in an amount ranging from 0.1 to 50% by weight based on the total weight of the coating layer or capsule layer. The amount may range from 0.1 to 40% by weight, or may range from 1 to 30% by weight.

The coating layer or capsule layer mentioned above can contain ingredient (C) in an amount ranging from 50 to 90% by weight based on the total weight of the coating layer or capsule layer. The amount may range from 50 to 80% by weight, or may range from 50 to 70% by weight.

The coating layer or capsule layer preferably further contains at least one selected from the group consisting of a water-soluble polymer other than polyethylene glycol and polyvinyl alcohol, a colorant, a lubricant, and wax.

Examples of the water-soluble polymer mentioned above include, for example, cellulose-based derivatives such as hypromellose (hydroxypropyl methylcellulose), methyl cellulose, hydroxypropyl cellulose, carboxymethyl cellulose sodium, hydroxyethyl methylcellulose, hydroxypropyl methylcellulose phthalate, and hydroxypropyl methylcellulose acetate succinate, starches such as starch and pullulan, water-soluble vinyl derivatives such as polyvinyl pyrrolidone, sodium alginate, gum arabic powder, gelatin and the like. Hypromellose, hydroxypropyl cellulose, water-soluble vinyl derivatives, and starches are preferable. Hypromellose, hydroxypropyl cellulose, and water-soluble vinyl derivatives are more preferable. Hypromellose and hydroxypropyl cellulose are most preferable. In addition, a mixture of a disintegrant auxiliary agent and an enteric polymer or a water-insoluble polymer may be contained, in addition to the water-soluble polymer. Examples of the enteric polymer include, for example, enteric cellulose esters such as cellulose acetate propionate, hydroxypropyl methylcellulose acetate succinate (for example, trade name: Shin-Etsu AQOAT, manufactured by Shin-Etsu Chemical Co., Ltd.), hydroxypropyl methylcellulose phthalate, carboxymethyl ethylcellulose, and cellulose acetate phthalate, enteric acrylic acid-based copolymers such as methacrylic acid copolymer L (for example, trade name: Eudragit L, manufactured by Evonik Degussa Japan), methacrylic acid copolymer LD (for example, trade name: Eudragit L 30D-55, manufactured by Evonik Degussa Japan, tradename: POLYQUID PA 30, POLYQUID PA 30-S, manufactured by Sanyo Chemical Industries, Ltd., trade name: Kollicoat MAE 30DP, manufactured by BASF), and methacrylic acid copolymer S (for example, trade name: Eudragit S, Eudragit S 100, Eudragit FS 30D, manufactured by Evonik Degussa Japan), and the like. These polymers may be used in a mixture of two or more types.

The water-soluble polymer is preferably hydroxypropyl methylcellulose. An amount of the water-soluble polymer mentioned above in the coating layer or capsule layer mentioned above is not particularly limited. The amount usually ranges from 50 to 99% by weight, preferably ranges from 60 to 95% by weight and more preferably ranges from 70 to 90% by weight based on the total weight of the coating layer or capsule layer.

The colorant mentioned above is preferably selected from the group consisting of titanium oxide, iron oxide, zinc oxide, tar pigments, and lake pigments.

Examples of iron oxide include, for example, black iron oxide, red ferric oxide, yellow ferric oxide, and the like. Examples of tar pigments include, for example, water-soluble edible tar pigments such as food yellow No. 5 and food blue No. 2. Examples of lake pigments include, for example, yellow No. 5 aluminum lake, and the like. A combination of two or more types among these may be used. Titanium oxide is preferable. The amount of the colorant in the coating layer or capsule layer mentioned above is not particularly limited, but usually ranges from 1 to 20% by weight, preferably ranges from 3 to 15% by weight, and more preferably ranges from 5 to 10% by weight, based on the total weight of the coating layer or capsule layer.

Examples of the lubricant include, for example, calcium stearate, glycerol monostearate, glyceryl palmitostearate, magnesium stearate, sodium stearyl fumarate, sucrose fatty acid ester, zinc stearate, stearic acid, talc, and the like. A combination of two or more types among these may be used. Talc is preferable. An amount of the lubricant in the coating layer and capsule layer is not particularly limited, but usually ranges from 0.1 to 20% by weight, preferably ranges from 0.5 to 15% by weight, and more preferably ranges from 1.0 to 10% by weight, based on the total weight of the coating layer or capsule layer.

Examples of the wax include, for example, carnauba wax, beeswax, stearic acid and the like. A combination of two or more types among these may be used. Carnauba wax is preferable. An amount of the wax in the coating layer or capsule layer is not particularly limited, but usually ranges from 0.01 to 10% by weight, preferably ranges from 0.05 to 1% by weight, and more preferably ranges from 0.05 to 0.1% by weight, based on the total weight of the coating layer or capsule layer.

The coating layer or capsule layer mentioned above can contain a plasticizer other than ingredient (b). The types of the plasticizer are not particularly limited. For example, (B) at least one type selected from the group consisting of propylene glycol, glycerol, glyceryl triacetate, triethyl acetyl citrate, dibutyl sebacate, diethyl phthalate, castor oil, a copolymer of propylene oxide and ethylene oxide, triacetin, triethyl citrate, and a mixture thereof (hereinafter, simply referred to as "ingredient (B)" in some cases) can be used.

In order to further prevent or reduce decomposition of ingredient (A) in the solid formulation of the present invention over time, in the case of the core mentioned above contacting the coating layer or capsule layer mentioned above, the coating layer or capsule layer mentioned above is free from ingredient (B), or alternatively, even if the coating layer or capsule layer mentioned above contains ingredient (B), the amount thereof is preferably 0.9% by weight or less, more preferably 0.8% by weight or less, even more preferably 0.6% by weight or less, even more preferably 0.4% by weight or less, and in particular, preferably 0.3% by weight or less, based on the total weight of the solid formulation. More particularly, in the case of the aforementioned core contacting the aforementioned coating layer or capsule layer, the coating layer or capsule layer can contain the aforementioned ingredient (B), for example, in an amount ranging from 0.1 to 40% by weight based on the total weight of the coating layer or capsule layer, and the amount thereof preferably ranges from 1 to 35% by weight, and more preferably ranges from 5 to 10% by weight.

The coating layer or capsule layer can contain a plasticizer other than the ingredient (B) and ingredient (b) mentioned above. Examples of the plasticizer mentioned above include, for example, polysorbates such as polysorbate 20, polysorbate 40, polysorbate 60, and polysorbate 80, and the like. The amount of the aforementioned plasticizer ranges, for example, from 1 to 20% by weight, preferably ranges from 3 to 15% by weight, and more preferably ranges from 5 to 10% by weight, based on the coating layer or capsule layer mentioned above.

A method for forming the coating layer or capsule layer is not particularly limited. In the case of the core directly contacting the coating layer or capsule layer, the coating layer or capsule layer may be directly formed on the surface of the core by means of a coating machine represented by HICOATER, new HICOATER, AQUA COATER (manufactured by Freund Corp.), DOREA COATER, POWREX COATER (manufactured by Powrex Corporation), or the like, a sugar-coating pan, a Wurster type coating machine, or the like. On the other hand, in the case of the core directly non-contacting the coating layer or capsule layer, at least one isolation layer mentioned above may be formed on the surface of the core by means of the aforementioned coating machine, and the coating layer or capsule layer can be formed on the surface of the isolation layer by means of the aforementioned coating machine. In addition, after forming the coating layer or capsule layer, an intraoral disintegration property can also be improved by humidification or the like.

The formation of the coating layer or capsule layer and the formation of the isolation layer are preferably carried out using an aqueous coating liquid. The aqueous coating liquid means an aqueous dispersion or solution of the constitutional ingredients of the coating layer or capsule layer or those of the isolation layer, and means a coating liquid containing of water or a mixed solution of water/water-soluble organic solvent, as a medium.

The water amount in the aqueous coating liquid is suitably determined in accordance with types and blending amounts of the ingredients and the amount of the water-soluble organic solvent added. The preferable water amount ranges, for example, from 5 to 1,000 parts by weight, preferably ranges from 7 to 100 parts by weight, and more preferably ranges from 8 to 50 parts by weight based on one part by weight of the constitutional ingredients of the isolation layer or the coating layer or capsule layer.

Examples of the water-soluble organic solvent which may be added to the aqueous coating liquid include, for example, methanol, ethanol, propyl alcohol, isopropyl alcohol, acetone, methyl ethyl ketone, dioxane, tetrahydrofuran, acetonitrile, and the like. In particular, ethanol is preferable. The amount of the water-soluble organic solvent added is determined in accordance with the types and blending amount of the ingredients, preferably ranges from 0 to 8.0 parts by weight, more preferably ranges from 0 to 2.4 parts by weight, even more preferably ranges from 0 to 1.3 parts by weight, and even more preferably ranges from 0 to 0.4 parts by weight based on one part by weight of water. In particular, the medium is preferably only water without adding a water-soluble organic solvent. Here, the medium which is only water means that only water is substantially used, and contamination of a small amount (for example 0.03 parts by weight or less based on one part by weight of water) of an organic solvent is acceptable.

The temperature of the exhaust gas temperature of the coating machine during the coating step is preferably controlled so that the temperature is higher than 30° C., but lower than 60° C. in the present invention. The coating step used herein means a step of applying the coating liquid on the core by means of a spray or the like, and during the step, ventilation is carried out. The exhaust gas temperature mentioned above is preferably 32° C. or higher, but 55° C. or lower, and more preferably 35° C. or higher, but 45° C. or lower. When the exhaust gas temperature mentioned above is 30° C. or lower, or alternatively 60° C. or higher, separation of a coating film may easily occur, roughness of the coating film may be increased, and therefore, a good coating film may not be formed in some cases.

Alternatively, in the present invention, the product temperature during the coating step is preferably controlled so that the product temperature is higher than 20° C., but lower than 56° C. Here, the product temperature during the coating step is the temperature of the core during the coating step. The product temperature can be measured by means of an infrared thermometer. The product temperature mentioned above is preferably 25° C. or higher, but 50° C. or lower, and more preferably 35° C. or higher, but 45° C. or lower. If the aforementioned product temperature is 20° C. or lower or 56° C. or higher, separation of the coating film may easily occur, roughness of the coating film may be increased, and a good coating film may not be formed in some cases.

During controlling of the exhaust gas temperature or the product temperature, the adjustment of the exhaust gas temperature or the product temperature can be carried out by adjusting, for example, the charge gas temperature, the amount of the charge gas, or the addition rate of the coating liquid (spraying rate and the like). In particular, controlling of the charge gas temperature is preferably carried out.

The application of the coating liquid may be carried out by pouring-and-adding or spraying, and spraying is preferable. In the case where, for example, 1 kg of uncoated tablets (250 mg/tablet) are subjected to spray coating by means of a ventilation type coating machine such as HICOATER (manufactured by Freund Corp.) or the like, the blast temperature may be set based on the exhaust temperature criteria, and the spray coating can be carried out in an air volume ranging from 1.5 to 3.5 m$^3$/min at a spray rate ranging from 5 to 50 g/min.

The particular structure of the solid formulation of the present invention is not particularly limited. For example, the solid formulation may be in the form of fine granules, granules, capsules, or tablets. In the case of tablets, from one to two dividing lines for making division of the tablet easy may be provided. The shape of the tablet is not particularly limited, and may be, for example, round, oval (any oblong except for perfect circle; oval, egg-shaped, elliptical cylinder shape, old gold coin-shaped, or the like), diamond-shaped, triangle, or the like. The solid formulation may be in the form of so-called specially shaped tablets. In the case of providing a dividing line, the dividing line shape may be any of flat groove type, U-shaped groove type, or V-groove type. In the case of the tablet being in an oval shape, the dividing line can be preferably formed along the minor axis of the tablet.

The solid formulation of the present invention is preferably in the form of a tablet or a capsule. In the case of a tablet, a film-coating agent is preferable.

The size of the tablet mentioned above is not particularly limited. In the case of the tablet being in a general-column shape, the diameter of the column preferably ranges from 5 to 11 mm, more preferably ranges from 5 to 10 mm, and even more preferably ranges from 5 to 9 mm. In the case of the tablet being a specially shaped tablet, the maximum length of the specially shaped tablet can range from 5 to 11 mm, more preferably ranges from 5 to 10 mm, and even more preferably ranges from 5 to 9 mm.

A second aspect of the present invention relates to a method for preventing or reducing coloration of a solid formulation containing a certain benzothia(dia)zepine derivative, characterized in that a combination of (b) polyethylene glycol and (C) polyvinyl alcohol is not added to the aforementioned solid formulation, or alternatively, in the case of adding a combination of (b) polyethylene glycol and (C) polyvinyl alcohol to the aforementioned solid formulation, the aforementioned benzothia(dia)zepine derivative is isolated from the combination of (b) polyethylene glycol and (C) polyvinyl alcohol.

The aforementioned benzothia(dia)zepine derivative is identical to the aforementioned ingredient (A) in the first aspect of the present invention. Therefore, hereinafter, it is referred to as ingredient (A).

The aforementioned polyethylene glycol (b) is identical to the aforementioned ingredient (b) in the first aspect of the present invention. Therefore, hereinafter, it is referred to as ingredient (b).

The aforementioned polyvinyl alcohol (C) is identical to the aforementioned ingredient (C) in the first aspect of the present invention. Therefore, hereinafter, it is referred to as ingredient (C).

In the case of the aforementioned ingredient (A) being isolated from the combination of the aforementioned ingredient (b) and ingredient (C), the amount of the aforementioned ingredient (b) and/or ingredient (C) contained in the solid formulation of the present invention is not limited.

On the other hand, in the case of the aforementioned ingredient (A) not being isolated from the combination of the aforementioned ingredient (b) and ingredient (C), that is, in the case of the aforementioned ingredient (A) being able to contact the combination of the aforementioned ingredient (b) and ingredient (C), the solid formulation is free from a combination of ingredient (b) and ingredient (C). Here, "free from ~" means that ~ is not substantially included in the solid formulation of the present invention. A trace amount of ingredient (b) and ingredient (C) may coexist within such a range that coloration of the solid formulation of the present invention is prevented or reduced. More particularly, even if ingredient (A) is able to contact the combination of ingredient (b) and ingredient (C), the aforementioned ingredient (b) may exist in an amount of less than 1.0% by weight based on the total weight of the solid formulation. In addition, less than 0.1% by weight, or less than 0.01% by weight of ingredient (b) may exist. In addition, even if ingredient (A) is able to contact the combination of ingredient (b) and ingredient (C), the aforementioned ingredient (C) may exist in an amount of less than 10% by weight based on the total weight of the solid formulation, or less than 5% by weight of ingredient (C) may exist, or less than 1% by weight of ingredient (C) may exist.

The explanation described above for the first aspect of the present invention can be applied to the solid formulation in the second aspect of the present invention. Therefore, for example, the amount of ingredient (A) in the solid formulation is not particularly limited, but the amount can range from 0.01 to 50% by weight, preferably ranges from 0.05 to 40% by weight, more preferably ranges from 0.1 to 30% by weight, even more preferably ranges from 0.2 to 20% by weight, even more preferably ranges from 0.5 to 10% by weight, and in particular, preferably ranges from 0.8 to 5% by weight, based on the total weight of the solid formulation.

In addition, the amount of the ingredient (A) mentioned above in the solid formulation is not particularly limited, can range from 0.1 to 100 mg, preferably ranges from 0.3 to 75 mg, more preferably ranges from 0.5 to 50 mg, even more preferably ranges from 0.8 to 30 mg, and in particular, preferably ranges from 1 to 20 mg.

In accordance with the present invention, in a solid formulation containing ingredient (A), the derivative mentioned above can be stabilized therein. Therefore, a solid formulation containing stabilized ingredient (A) can be provided.

Ingredient (A) in the solid formulation mentioned above is stable over time even under an atmosphere of high temperature and/or high humidity. Therefore, even if the solid formulation of the present invention is present under an atmosphere of high temperature and/or high humidity, occurrence of coloration (in particular, red coloration) of the solid formulation due to destabilization of the ingredient (A) mentioned above can be prevented or reduced. In particular, in accordance with the present invention, the solid formulation can be stable in a well-closed environment.

Therefore, in accordance with the present invention, the solid formulation can be stored for a long period of time, and the pharmaceutical effects of the ingredient (A) mentioned above contained in the solid formulation can be maintained. In particular, in accordance with the present invention, the solid formulation containing the ingredient (A) mentioned above can be stable even under an atmosphere of high temperature and high humidity in the summer season.

INDUSTRIAL APPLICABILITY

The present invention can provide a stabilized solid formulation containing a specified benzothia(dia)zepine derivative. The specific benzothia(dia)zepine derivatives mentioned above can function as an IBAT inhibitor, and for this reason, the solid formulations according to the present invention are useful for a long period of time in the treatment of dyslipidemic conditions and disorders such as hyperlipidemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL), as well as in the treatment of functional constipation or constipation-predominant irritable bowel syndrome.

EXAMPLES

Hereinafter, the present invention is described in detail with reference to Examples and Comparative Examples. It should be understood that the present invention is not limited to these Examples.

Reference Examples 1 to 9

1,1-dioxo-3,3-dibutyl-5-phenyl-7-methylthio-8-(N—{(R)-1'-phenyl-1'-[N'-(carboxymethyl)carbamoyl]methyl}carbamoylmethoxy)-2,3,4,5-tetrahydro-1,5-benzothiazepine (Elobixibat) and an additive shown in Table 1 were mixed so that they have a volume ratio of 1:1 based on visual quantities, and thereby, the mixtures according to Reference Examples 3 to 9 were obtained. In Reference Examples 8 and 9, two types of additives shown in Table 1 were mixed in a weight ratio of 1:1, and the obtained mixture was further mixed with Elobixibat so that they had a volume ratio of 1:0.5 based on visual quantities. The mixture of each of Reference Examples 3 to 9, only Elobixibat as Reference Example 1, and only Macrogol (polyethylene glycol) 6000 as Reference Example 2 were independently stored in an aluminum bag as an airtight container for 2 weeks under the conditions of 60° C. and 75% relative humidity. After storage, the presence or absence of coloration of the materials of Reference Examples 1 and 2 and the mixtures according to Reference Examples 3 to 9 was visually observed. The results are shown in Table 1.

TABLE 1

| | Mixture | | Coloration after storage |
|---|---|---|---|
| | Drug substance | Additive(s) | Before storage → after storage |
| Reference Example 1 | Elobixibat | — | — | Not observed white → white |
| Reference Example 2 | — | Macrogol 6000 | — | Not observed White → white |
| Reference Example 3 | Elobixibat | Polyvinyl alcohol partial-saponification product | — | Not observed White → white |
| Reference Example 4 | Elobixibat | Hypromellose | — | Not observed White → white |
| Reference Example 5 | Elobixibat | Talc | — | Not observed White → white |
| Reference Example 6 | Elobixibat | Titanium oxide | — | Not observed White → white |
| Reference Example 7 | Elobixibat | Macrogol 6000 | — | Observed White → pale yellow |
| Reference Example 8 | Elobixibat | Macrogol 6000 | Titanium oxide | Observed White → pale yellow |
| Reference Example 9 | Elobixibat | Polyvinyl alcohol partial-saponification product | Macrogol 6000 | Observed White → pale pink |

As is clear from Table 1, in Elobixibat alone (Reference Example 1) or Macrogol 6000 alone (Reference Example 2), coloration was not observed. In addition, in the mixture of Elobixibat with polyvinyl alcohol partial-saponification product (Reference Example 3), Hypromellose (Reference Example 4), Talc (Reference Example 5) or titanium oxide (Reference Example 6), coloration was not observed.

On the other hand, in the ternary system mixture of Elobixibat, polyvinyl alcohol partial-saponification product, and Macrogol 6000 (Reference Example 9), coloration to pale pink occurred.

In the binary system mixture of Elobixibat and Macrogol 6000 (Reference Example 7) and the ternary system mixture of Elobixibat, Macrogol 6000 and titanium oxide (Reference Example 8), slight coloration to pale yellow was observed, but was not light pink as observed in Reference Example 9.

Therefore, it can be seen that coloration to red in an Elobixibat-containing formulation is caused by contacting Elobixibat with a combination of polyethylene glycol and polyvinyl alcohol.

Examples 1 to 4 and Comparative Examples 1 and 2

Crystalline cellulose (filler), D-mannitol (filler), Hypromellose (binder), croscarmellose sodium (disintegrant), light anhydrous silicic acid (fluidizer), magnesium stearate (lubricant), and 1,1-dioxo-3,3-dibutyl-5-phenyl-7-methylthio-8-(N—{(R)-1'-phenyl-1'-[N'-(carboxymethyl)carbamoyl]methyl}carbamoylmethoxy)-2,3,4,5-tetrahydro-1,5-benzothiazepine (Elobixibat) were formulated into tablets in accordance with a conventional method (mixing in a bag or mixing by means of a rotatory mixer, and tableting by means of a rotary tableting machine). Thereby, uncoated tablets (weight of uncoated tablet: 110 mg or 320 mg) containing 5% by weight of Elobixibat (drug substance) were obtained.

Macrogol 6000 (plasticizer), and Hypromellose (coating agent) or polyvinyl alcohol partial-saponification product (coating agent) were added to purified water, and mixed well until the mixture was dissolved. After the mixture was dissolved, titanium oxide (colorant) was added thereto, and mixed well to disperse it therein. The obtained mixture liquid was used as a film coating liquid. The compositions of the film coatings according to Examples 1 to 4 and Comparative Examples 1 and 2 are shown in Table 2.

The aforementioned film coating liquid was sprayed onto the aforementioned uncoated tablets by means of a pan-type coating machine. Thereby, the film coating tablets according to Examples 1 and 3, Comparative Example 1 and Comparative Example 2 were obtained.

On the other hand, Hypromellose was added to purified water and mixed well until it was dissolved. Thereby, the solution was used as a shielding coating liquid. The shielding coating liquid was sprayed onto the uncoated tablets by means of a pan-type coating machine, and shielding coating was carried out. Subsequently, the aforementioned film coating liquid containing polyvinyl alcohol was sprayed onto the tablets which had been subjected to shielding coating. Thereby, the film coating tablets according to Example 2 and Example 4, in which a shielding coating layer (isolation layer) was provided, were obtained.

The obtained film coating tablets in accordance with each of Examples 1 to 4 and Comparative Examples 1 and 2 were stored in an aluminum bag as an airtight container for 2 weeks under the conditions of 60° C. and 75% relative humidity. The outer appearance of the tablets before and after storage was observed, and the coloration state thereof was evaluated. The results are shown in Table 2.

TABLE 2

| | | Example 1 | Example 2 | Example 3 | Example 4 | Comparative Example 1 | Comparative Example 2 |
|---|---|---|---|---|---|---|---|
| Weight of uncoated tablets | [mg/tablet] | 110 | 110 | 320 | 320 | 110 | 320 |
| Total weight of shielding coating | | — | 3.2 | — | 18.2 | — | — |
| Total weight of film coating | | 2.1 | 4.2 | 8.1 | 17.1 | 4.5 | 16.7 |
| Composition of film coating part | Hypromellose | [parts by weight] | 63 | — | 63 | — | — | — |
| | polyvinyl alcohol partial-saponification product | | — | 63 | — | 63 | 63 | 63 |
| | Macrogol6000 | | 31 | 31 | 31 | 31 | 31 | 31 |
| | Titanium oxide | | 6 | 6 | 6 | 6 | 6 | 6 |
| Coloration after storage for 2 weeks Before storage → after storage | — | Not observed White → white | Not observed Cream color → cream color | Not observed White → white | Not observed Cream color → cream color | Observed White → slightly pale pink | Observed White → slightly pale pink |

As is clear from Table 2, in Comparative Example 1 and Comparative Example 2, in which the film coating contained a combination of polyvinyl alcohol partial-saponification product and Macrogol 6000, and the aforementioned film coating contacted uncoated tablets, the surface of the tablets was colored to pale pink.

On the other hand, in Example 1 and Example 3 in which the film coating did not contain a combination of polyvinyl alcohol partial-saponification product and Macrogol 6000, and the aforementioned coating film contacted the uncoated tablets, no red coloration at the surface of the tablets was observed. In addition, even in the case of the film coating containing both polyvinyl alcohol partial-saponification product and Macrogol 6000, in Example 2 and Example 4, in which a shielding coating layer was provided between the uncoated tablets and the film coating, controlling of coloration could be carried out.

What is claimed is:

1. A solid formulation characterized by comprising:
   (A) 1,1-dioxo-3,3-dibutyl-5-phenyl-7-methylthio-8-(N—{(R)-1'-phenyl-1'-[N'-(carboxymethyl)carbamoyl]methyl}carbamoylmethoxy)-2,3,4,5-tetrahydro-1,5-benzothiazepine, or a pharmaceutically acceptable salt, solvate, or solvate of such a salt, wherein the solid formulation comprises:
   one core, wherein said core is a homogenous mixture comprising ingredient (A), and
   one coating layer or capsule layer enclosing at least a part of said core, wherein said coating layer or capsule layer comprises (C) polyvinyl alcohol and does not comprise (b) polyethylene glycol
   wherein said coating layer or capsule layer comprises said ingredient (C) in an amount ranging from 50 to 90% by weight based on the total weight of the coating layer or capsule layer.

2. The solid formulation according to claim 1, wherein said coating layer or capsule layer is present in a ratio ranging from 1 to 20% by weight based on the total weight of the solid formulation.

3. The solid formulation according to claim 1, wherein said coating layer or capsule layer further comprises at least one selected from the group consisting of a water-soluble polymer other than polyethylene glycol or polyvinyl alcohol, a colorant, a lubricant, and a wax.

4. The solid formulation according to claim 3, wherein said water-soluble polymer is hydroxypropyl methylcellulose.

5. The solid formulation according to claim 3, wherein said colorant is selected from the group consisting of titanium oxide, iron oxide, zinc oxide, tar pigment, and lake pigment.

6. The solid formulation according to claim 3, wherein said lubricant is talc.

7. The solid formulation according claim 3, wherein said wax is carnauba wax.

8. The solid formulation according to claim 3, which is a film coating tablet or a capsule.

9. The solid formulation according to claim 1, wherein said core comprises at least one additive selected from the group consisting of a filler, a disintegrant, a binder, a lubricant, and a fluidizer.

10. The solid formulation according to claim 9, wherein the solid formulation comprises the filler in an amount ranging from 60% to 99% by weight based on the total weight of the solid formulation.

11. The solid formulation according to claim 1, wherein the amount of said ingredient (A) ranges from 0.01 to 50% by weight based on the total weight of the solid formulation.

12. The solid formulation according to claim 1, wherein the amount of said ingredient (A) ranges from 1 to 20 mg.

13. The solid formulation according to claim 1, which is in the form of a tablet having a diameter ranging from 5 to 11 mm.

14. The solid formulation according to claim 1, which is intended for treating or preventing constipation in a warm-blooded animal including a human being.

15. The solid formulation according to claim 14, wherein the constipation is functional constipation or constipation-predominant irritable bowel syndrome.

* * * * *